US011311343B2

(12) United States Patent
Lwin et al.

(10) Patent No.: US 11,311,343 B2
(45) Date of Patent: Apr. 26, 2022

(54) FLEXIBLE ROBOTIC ENDOSCOPY SYSTEM

(71) Applicants: ENDOMASTER PTE LTD, Singapore (SG); HOYA CORPORATION, Tokyo (JP)

(72) Inventors: Tae Zar Lwin, Singapore (SG); Isaac David Penny, Singapore (SG); Christopher Lee Shih Hao Sam Soon, Singapore (SG); Tomonori Yamamoto, Singapore (SG); Naoyuki Naito, Tokyo (JP); Tetsu Hirayama, Tokyo (JP); Takahiro Kobayashi, Tokyo (JP)

(73) Assignees: ENDOMASTER PTE LTD, Singapore (SG); HOYA CORPORATION, Tokyo (JP)

( * ) Notice: Subject to any disclaimer, the term of this patent is extended or adjusted under 35 U.S.C. 154(b) by 278 days.

(21) Appl. No.: 15/760,399

(22) PCT Filed: Sep. 16, 2016

(86) PCT No.: PCT/SG2016/050449
§ 371 (c)(1),
(2) Date: Mar. 15, 2018

(87) PCT Pub. No.: WO2017/048194
PCT Pub. Date: Mar. 23, 2017

(65) Prior Publication Data
US 2019/0053861 A1 Feb. 21, 2019

Related U.S. Application Data

(60) Provisional application No. 62/220,209, filed on Sep. 17, 2015.

(51) Int. Cl.
*A61B 1/015* (2006.01)
*A61B 1/018* (2006.01)
(Continued)

(52) U.S. Cl.
CPC .............. *A61B 34/30* (2016.02); *A61B 1/005* (2013.01); *A61B 1/00039* (2013.01);
(Continued)

(58) Field of Classification Search
CPC ......................... A61B 1/00006; A61B 1/00091
(Continued)

(56) References Cited

U.S. PATENT DOCUMENTS 5,894,322 A * 4/1999 Hamano ............ A61B 1/00006
348/65
2006/0173244 A1 * 8/2006 Boulais ................ A61B 1/0676
600/156

(Continued)

FOREIGN PATENT DOCUMENTS

JP 2000325361 11/2000
JP 2004243136 9/2004

OTHER PUBLICATIONS

International Application No. PCT/SG2016/050449, International Search Report and Written Opinion dated Jan. 10, 2017.
(Continued)

*Primary Examiner* — Alexandra L Newton
*Assistant Examiner* — Rynae E Boler
(74) *Attorney, Agent, or Firm* — Kilpatrick Townsend & Stockton LLP

(57) ABSTRACT

An embodiment of the invention is an endoscopy system with newly designed docking block, brake control, wire tension adjustment, bending angle sensor, memory chip data storage, valve control, imaging lens cleaning, optimized lumen arrangement and distal position sensor. The docking block can have a one-touch retaining mechanism. Braking control can be accessed by the endoscopist at the hand grip or knobs. Wire tension can be relaxed or tightened in response to surgeon or endoscopist control. Bending angle (Continued)

sensors can protect surgical instruments. Memory chip can store usage data of the endoscope. Multiple valves can have priority control. Lenses can be cleaned with one touch of a button. Lumens can be arranged to maximize imaging and lighting angles. Position markers accompanied with sensors can position the distal end of the endoscope automatically in the optimal position.

6 Claims, 26 Drawing Sheets

(51) Int. Cl.

| | | |
|---|---|---|
| *A61B 1/05* | (2006.01) | |
| *A61B 34/30* | (2016.01) | |
| *A61B 1/005* | (2006.01) | |
| *A61B 1/00* | (2006.01) | |
| *A61B 1/012* | (2006.01) | |
| *A61B 1/06* | (2006.01) | |
| *A61B 34/20* | (2016.01) | |

(52) U.S. Cl.
CPC ........ *A61B 1/0052* (2013.01); *A61B 1/00068* (2013.01); *A61B 1/00124* (2013.01); *A61B 1/00128* (2013.01); *A61B 1/015* (2013.01); *A61B 1/018* (2013.01); *A61B 1/0125* (2013.01); *A61B 1/05* (2013.01); *A61B 1/0676* (2013.01); *A61B 2034/2072* (2016.02); *A61B 2034/301* (2016.02)

(58) Field of Classification Search
USPC .................................................. 600/159, 156
See application file for complete search history.

(56) References Cited

U.S. PATENT DOCUMENTS

| | | | |
|---|---|---|---|
| 2006/0178559 A1* | 8/2006 | Kumar | G09B 23/28 600/109 |
| 2008/0051629 A1* | 2/2008 | Sugiyama | A61B 1/018 600/114 |
| 2009/0171150 A1* | 7/2009 | Iede | A61B 1/018 600/112 |
| 2009/0287043 A1 | 11/2009 | Naito et al. | |
| 2013/0046280 A1* | 2/2013 | Martin | G06F 19/3462 604/503 |
| 2013/0172828 A1* | 7/2013 | Kappel | A61B 17/320016 604/272 |
| 2015/0148599 A1 | 5/2015 | Wilson et al. | |

OTHER PUBLICATIONS

U.S. Appl. No. 16/946,374, Non-Final Office Action, dated Nov. 25, 2020, 7 pages.
U.S. Appl. No. 16/946,374, Final Office Action, dated Mar. 16, 2021, 7 pages.

* cited by examiner

4

4

3C-100

6A-100

6C-100

6D-100

7B-100

FLEXIBLE ROBOTIC ENDOSCOPY SYSTEM

TECHNICAL FIELD

The present disclosure relates to a flexible robotic endoscopy system that includes an endoscope body and a flexible elongate shaft extending therefrom into which at least one tendon driven robotic endoscopic instrument is insertable; a docking station or endoscope docking system with which the endoscope body is releasably dockable; and a translation mechanism operable to selectively longitudinally displace the endoscopic instrument(s) within the flexible elongate shaft when the endoscope body is docked. The present disclosure further relates to various improvements to the flexible robotic endoscopy system, particularly the inclusion of a docking block; control of a docking station brake; adjustment and/or relaxation of wire tension; surgical instrument damage protection through bending angle sensing; the inclusion of a memory chip in the endoscope; the inclusion of a valve controller box; a cleaning mechanism for an imaging-related lens (e.g. of an imaging endoscope); arrangements of particular lumens; and surgical instrument distal position sensor(s) of the endoscopy system.

DETAILED DESCRIPTION

Figure 1A:
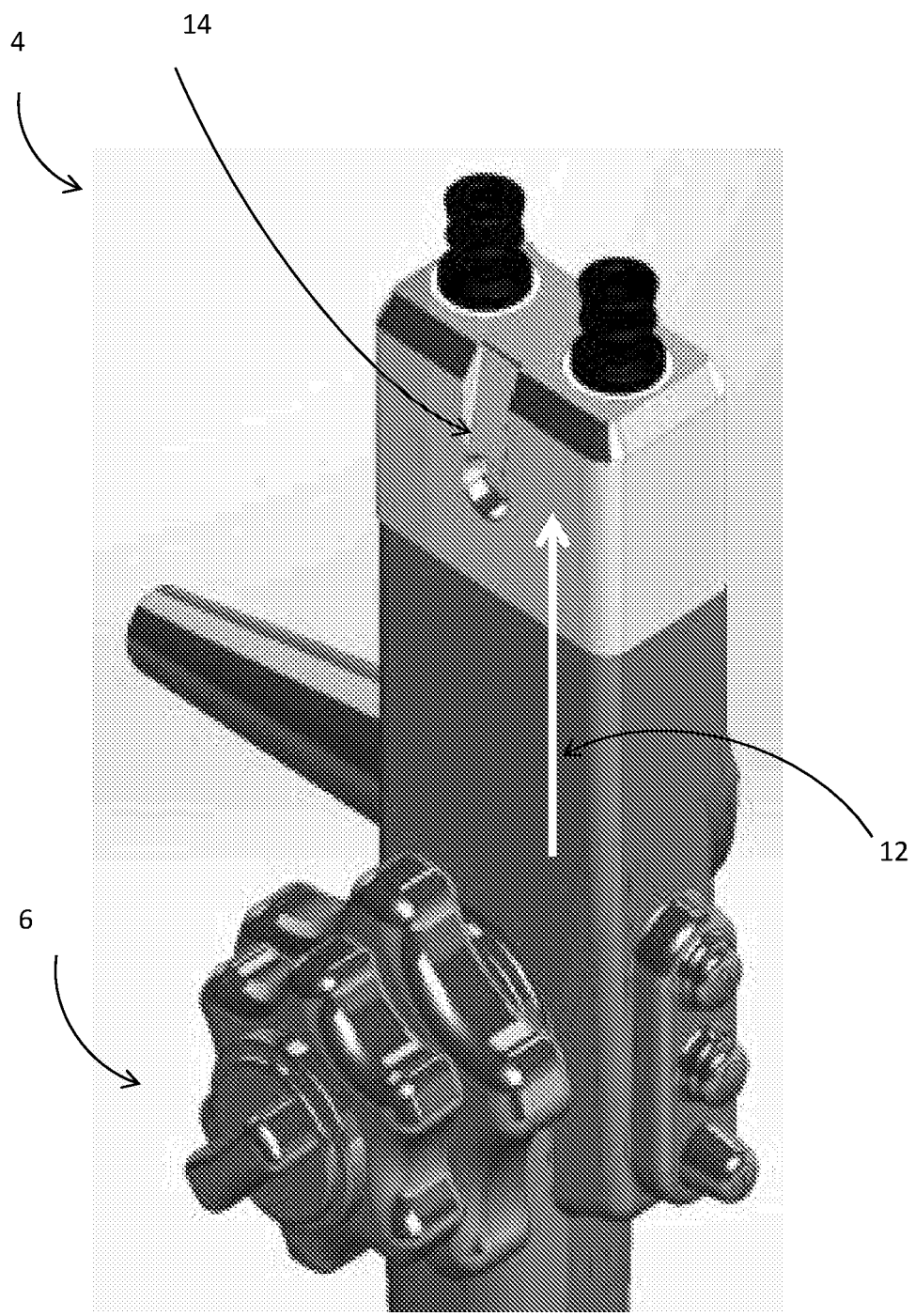
FIGS. 1A-1D are illustrations relating to a docking block for the endoscopy system, in accordance with an embodiment of the present disclosure.
Figure 1B:
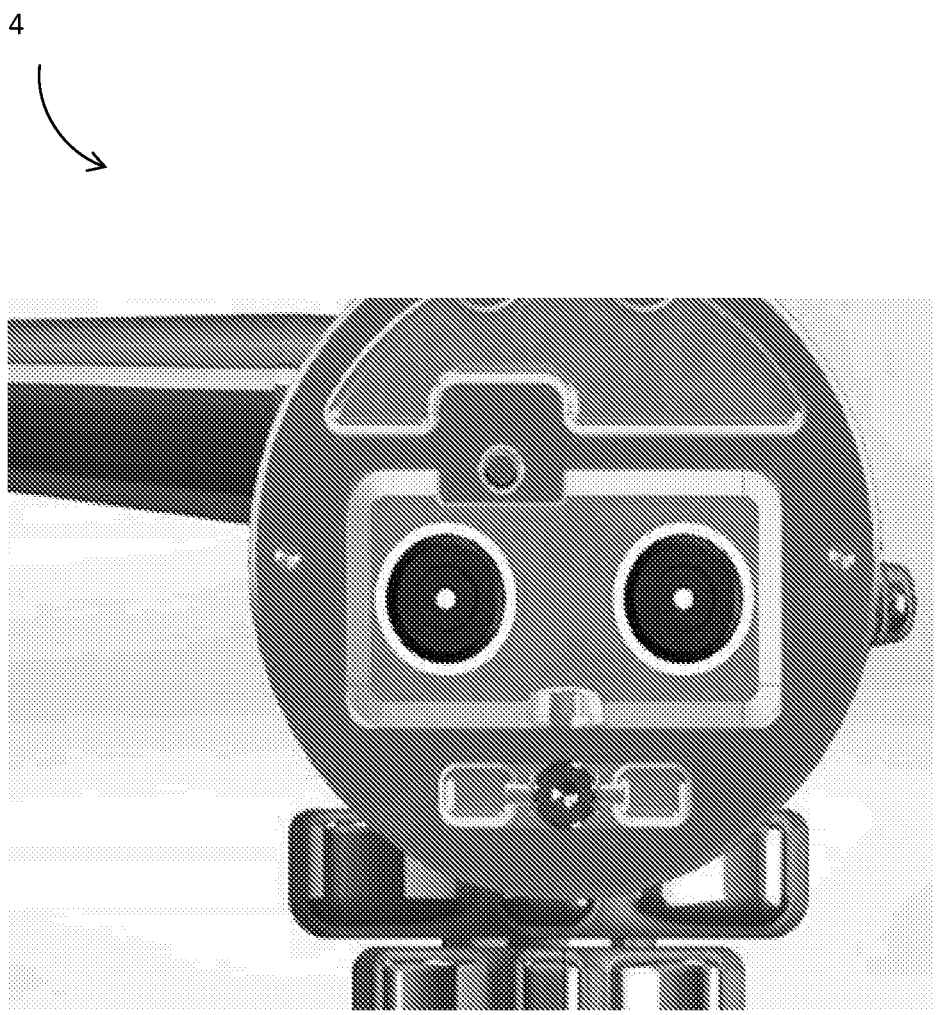

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "I" in a FIG. or associated text is understood to mean "and/or" unless otherwise indicated. The recitation of a particular numerical value or value range herein is understood to include or be a recitation of an approximate numerical value or value range, for instance, within +/−20%, +/−15%, +/−10%, or +/−5%.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

Representative Embodiments of an Endoscopy System

Embodiments in accordance with the present disclosure are directed to master-slave flexible robotic endoscopy systems, which include a master-side system and a slave-side system that is controllable or controlled by the master-side system. Depending upon embodiment details, one or more portions of a master-slave flexible robotic endoscopy system in accordance with the present disclosure can correspond or be analogous to or include one or more types of elements, structures, and/or devices described (a) in International Patent Application No. PCT/SG2013/000408; and/or (b) International Patent Publication No. WO 2010/138083.

A master-slave flexible robotic endoscopy system in accordance with an embodiment of the present disclosure includes a master/master system/master-side system (e.g. surgeon console unit) having master-side elements associated therewith, and a slave/slave system/slave-side system (e.g. patient-side cart system) having slave-side elements associated therewith.

There is a distal end of an endoscopy apparatus disposed at a slave or slave-side system, in various embodiments, the master system and the slave system are configured for signal communication with each other such that the master system can issue commands to the slave system and the slave system can precisely control, maneuver, manipulate, position, and/or operate (a) a set of robotic arms and corresponding end effectors carried or supported by an endoscope (also referred to herein as a transport endoscope) of the slave system, and possibly (b) an imaging endoscope or imaging probe member carried or supported by the transport endoscope, in response to master system inputs. In some embodiments, the transport endoscope does not include the imaging endoscope in order to reduce the outer diameter of the transport endoscope. This would be useful to keep the transport endoscope smaller for insertion into the body, and to make the transport endoscope more flexible for maneuverability. In lieu of the imaging endoscope, the transport endoscope may have a camera lens or a small imaging device disposed at the distal end of the transport endoscope.

In various embodiments, the imaging endoscope or imaging probe member is typically configured for at least surge displacement and possibly also roll motion (e.g., about a central or longitudinal axis of the imaging endoscope or imaging probe member) in response to control signals received from the master system and/or a set of control's carried by the transport endoscope. In some embodiments, the imaging endoscope/imaging probe member is configured for heave, sway, and/or pitch motion, such as by way of internally carried tendons, in which case the imaging endoscope/imaging probe member can be referred to as a robotically controlled imaging endoscope/imaging probe member. Control signals for spatially manipulating a robotically controlled imaging endoscope/imaging probe member can be generated by the master system, and/or a set of slave system controls, such as control buttons, switches, a joystick, or the like carried by the transport endoscope.

The master and slave systems can further be configured such that the slave system can dynamically provide tactile/haptic feedback signals (e.g., force feedback signals) to the master system as the robotic arms and/or end effectors associated therewith are positioned, manipulated, or operated. Such tactile/haptic feedback signals are correlated with or correspond to forces exerted upon the robotic arms and/or end effectors within an environment in which the robotic arms and end effectors reside.

Various embodiments in accordance with the present disclosure are directed to surgical situations or environments, for instance, Natural Orifice Transluminal Endoscopic Surgery (NOTES) procedures performed upon a patient or subject while they are disposed on a surgical table or platform. In such embodiments, at least portions of the slave system are configured to reside within an endoscopy room, Operating Theatre (OT) or Operating Room (OR). Depending upon embodiment details, the master system can reside within or outside of (e.g., near or remote from) the endoscopy room, OT, or OR. Communication between the master system and the slave system can occur directly (e.g., through a set of local communication lines, and/or local wireless communication), or indirectly by way of one or more networks (e.g., a Local Area Network (LAN), a Wide Area Network (WAN), and/or the Internet) in accordance with embodiment details.

In an embodiment, the master system includes a frame or console structure that carries left and right surgeon console manipulators or haptic input devices a set of additional/auxiliary hand-operated input devices/buttons; a set of foot operated controls or pedals; a display device; and a processing module. The frame/console structure can include a set of wheels such that the master system is readily portable/positionable within an intended usage environment (e.g., an OT/OR, or a room external to or remote therefrom); and a set of arm supports. During a representative endoscopy procedure, a surgeon positions or seats themselves relative to the master system such that their left and right hands can hold or interact with the left and right haptic input devices and their feet can interact with the pedals. The processing module processes signals receive from the haptic input devices, the additional/auxiliary hand-operated input devices, and the pedals, and issues corresponding commands to the slave system for purpose of manipulating/positioning/controlling the robotic arms and the end effectors corresponding thereto, and possibly manipulating/positioning/controlling the imaging endoscope. The processing module can additionally receive tactile/haptic feedback signals from the slave system, and conveys such tactile/haptic feedback signals to the surgeon console manipulators/haptic input devices Representative manners of generating tactile/haptic feedback signals are described in detail in International Patent Application No. WO 2010/138083. The processing module includes computing/processing and communication resources (e.g., one or more processing units, memory/data storage resources including Random Access Memory (RAM) Read-only Memory (ROM), and possibly one or more types of disk drives, and a serial communication unit and/or network communication unit) in a manner readily understood by one having ordinary skill in the relevant art.

In an embodiment, the slave system includes an endoscope or a transport endoscope having a flexible elongate shaft; an endoscope docking system/a docking station to which the transport endoscope can be selectively/selectably coupled (e.g., mounted/docked and dismounted/undocked); an imaging subsystem; an endoscopy support function subsystem and an associated valve control unit or valve controller box (VCB); an actuation unit or motorbox; and a main control unit. In several embodiments, the slave system additionally includes a patient-side cart, stand, or rack configured for carrying at least some slave system elements. The patient-side cart typically includes wheels to facilitate easy portability and positioning of the slave system (e.g., at a desired location within an OT/OR).

In brief, the imaging subsystem facilitates the provision or delivery of illumination to the imaging endoscope, as well as the processing and presentation of optical signals captured by the imaging endoscope. The imaging subsystem includes an adjustable display device configured for presenting (e.g., on a real-time basis) images captured by way of the imaging endoscope, in a manner readily understood by one having ordinary skill in the relevant art. The endoscopy support function subsystem in association with the valve controller box facilitates the selective controlled provision of insufflation or positive pressure, suction or negative/vacuum pressure, and irrigation to the transport endoscope, as also readily understood by one having ordinary skill in the relevant art. The actuation unit/motorbox provides a plurality of actuators or motors configured for driving the robotic arms and the end effectors under control of the main control unit, which includes a set of motor controllers.

The main control unit additionally manages communication between the master system and the slave system, and processes input signals received from the master system for purpose of operating the robotic arms and end effectors in a manner that directly and precisely corresponds to surgeon manipulation of the master system's haptic input devices. In multiple embodiments, the main control unit additionally generates the aforementioned tactile/haptic feedback signals, and communicates such tactile/haptic feedback signals to the master system on a real-time basis. Representative manners of generating tactile/haptic feedback signals are described in detail in International Patent Application No. WO 2010/138083. The main control unit includes signal/data processing, memory/data storage, and signal communication resources (e.g., one or more microprocessors, RAM, ROM, possibly a solid state or other type of disk drive, and a serial communication unit and/or network interface unit) in a manner readily understood by one having ordinary skill in the relevant art.

Flexible elongate assemblies which can be inserted to or withdrawn from the transport endoscope in accordance with an embodiment of the present disclosure. The flexible elongate assemblies may comprise the actuation assemblies and a flexible imaging endoscope assembly.

The actuation assemblies may be, include, or attached with robotic arms/surgical instruments/robotic surgical instruments. Some examples include a grasper, and a cautery spatula, in accordance with an embodiment of the present disclosure. Also, flexible imaging endoscope assembly may be an imaging endoscope probe in accordance with an embodiment of the present disclosure.

The transport endoscope comprises a main body at a proximal end and a flexible elongate shaft extends toward a distal end. The transport endoscope additionally includes an endoscopy support function connector assembly by which the transport endoscope's main body can be coupled to the valve controller box, in a manner readily understood by one having ordinary skill in the relevant art. The main body may be made of rigid material(s) such as hard plastics or metals and the flexible elongate shaft is made of flexible materials such as rubber, rubber-like, and/or soft plastic materials.

The main body includes or defines a proximal portion, border, surface, or end of the transport endoscope, and provides a plurality of insertion inlets through which channels or passages that extend within and along the transport endoscope's flexible elongate shaft are accessible. The main body comprises a proximal end portion or proximal end and a distal end portion or distal end, and a housing that extends between or from the proximal end to the distal end. The housing comprises a plurality of surfaces and the plurality of insertion inlets. The plurality of insertion inlets is carried by the proximal end of the main body, for instance, such that the plurality of insertion inlets resides on at least one surface of the housing at the main body's proximal end (e.g., a top surface or a set of top surfaces of the housing at the main body's proximal end).

In several embodiments, the main body additionally provides a control interface for the transport endoscope, by which an endoscopist can exert navigational control over the transport endoscope's flexible elongate shaft. For instance, the main body can include a number of control elements, such as one or more buttons, knobs, switches, levers, joysticks, and/or other control elements to facilitate endoscopist control over transport endoscope operations, in a manner readily understood by one having ordinary skill in the relevant art.

The flexible elongate shaft is configured to extend away from the distal end of the main body and terminate at a distal end of the transport endoscope. The flexible elongate shaft comprises a proximal end, a distal end, a central axis (not illustrated) and a plurality of channels therewithin for carrying portions of flexible elongate assemblies and an opening disposed at, proximate, or near the flexible elongate shaft's distal end for each of the plurality of channels.

The plurality of channels may comprise a set of instrument channels which carry actuation assemblies. In various embodiments, the channels may also comprise passages for enabling the delivery of insufflation or positive pressure, suction or vacuum pressure, and irrigation to an environment in which the distal end of the flexible elongate shaft resides.

Each actuation assembly typically corresponds to a given type of endoscopic tool. For instance, in a representative implementation, a first actuation assembly can carry a first robotic arm having a grasper or similar type of end effector; and a second actuation assembly can carry a second robotic arm having a cautery spatula or similar type of cauterizing end effector. The set of instrument channels includes at least one channel configured for carrying portions of a flexible actuation assembly that can be inserted into and withdrawn from the transport endoscope Each actuation assembly includes a robotic arm and an end effector corresponding thereto; flexible control elements, tendon elements, or tendons by which the robotic arm and the end effector can be positioned or manipulated in accordance with a predetermined number of DOF; and an interface or adapter by which the actuation assembly's flexible tendons can be mechanically coupled to and decoupled from specific actuators within the motorbox. In various embodiments, each tendon resides within a corresponding flexible sheath (e.g., a helical coil). In some embodiments, the actuation assembly can be disposable.

In an embodiment, a given actuation assembly includes a robotic arm and its corresponding end effector a flexible elongate outer sleeve and/or coil that internally carries a plurality of tendon/sheath elements, such that tension or mechanical forces can be selectively applied to particular tendon elements for precisely manipulating and controlling the operation of the robotic arm and/or the end effector; and an instrument input adapter by which tendons within the outer sleeve can be mechanically coupled to corresponding actuators within the motorbox, as further detailed below. Representative types of tendon/sheath elements, robotic arms and end effectors as well as representative manners in which tendon elements can couple to and control portions of a robotic arm (e.g., joints/joint primitives) and/or a corresponding end effector to provide maneuverability/manipulability relative to available DOFs are described in detail in (a) International Patent Application No. PCT/SG2013/000408; and/or (b) International Patent Publication No. WO 2010/138083. A given tendon and its corresponding sheath can be defined as a tendon/sheath element.

The robotic arm, end effector, and portions of the outer sleeve/coil can be inserted into an instrument channel of the transport endoscope's flexible elongate shaft, such that the robotic arm and the end effector reach or approximately reach, and can extend a predetermined distance beyond, the distal end of the flexible elongate shaft. As described in detail below, the actuation assembly's outer sleeve/coil, and hence the robotic arm and end effector, can be selectively longitudinally translated or surged (i.e., displaced distally or proximally with respect to the distal end of the flexible elongate shaft) by way of a translation module, unit, stage, or mechanism such that the proximal-distal positions of the robotic arm and the end effector relative to the distal end of the flexible elongate shaft can be adjusted within an environment beyond the distal end of the flexible elongate shaft, up to a predetermined maximum distance away from the distal end of the flexible elongate shaft, for purpose of carrying out an endoscopic procedure.

In particular embodiments, the actuation assembly includes a collar element, collet, or band that surrounds at least a portion of the outer sleeve/coil at a predetermined distance away from the distal tip of the end effector. As detailed below, the collar element is designed to matingly engage with a receiver of the translation mechanism, such that longitudinal/surge translation of the collar element across a given distance relative to the distal end of the flexible elongate shaft results in corresponding longitudinal/surge translation of the robotic arm and end effector.

In several embodiments, the plurality of channels provided within the transport endoscope's flexible elongate shaft additionally include an imaging endoscope channel, which is configured for carrying portions of a flexible imaging endoscope assembly that can be inserted into and/or withdrawn from the transport endoscope. In a manner analogous or generally analogous to that described above for the actuation assembly, in an embodiment the imaging endoscope assembly includes a flexible outer sleeve, coil, or shaft that surrounds or forms an outer surface of the flexible imaging endoscope; an imaging input adapter by which a set of tendons corresponding to or within the imaging endoscope can be mechanically coupled to corresponding actuators within the motorbox such that a distal portion of the imaging endoscope can be selectively maneuvered or positioned in accordance with one or more DOFs (e.g., heave and/or sway motion) within an environment at, near, and/or beyond the distal end of the flexible elongate shaft; and an imaging connector assembly by which electronic and/or optical elements (e.g., optical fibers) of the imaging endoscope can be respectively electronically and/or optically coupled to an image processing unit of the imaging subsystem. For instance, in some embodiments the imaging endoscope can include or be coupled to tendons such that a distal end or face of the imaging endoscope can selectively/ selectably capture anterograde and retrograde images of the robotic arms and end effectors during an endoscopic procedure. Representative embodiments of imaging endoscopes and control elements such as tendons associated therewith that can be incorporated into an imaging endoscope assembly in accordance with an embodiment of the present disclosure are described in International Patent Application No. PCT/SG2013/000408 hereto. In some embodiments, the imaging endoscope assembly can be disposable.

In a manner identical, essentially identical, or analogous to that for the actuation assembly, the outer sleeve of the imaging endoscope assembly, and hence the distal end of the imaging endoscope, can be selectively longitudinally translated/surged relative to the distal end of the flexible elongate shaft by way of the translation mechanism, such that the longitudinal or proximal-distal position of the imaging endoscope can be adjusted at, near, and/or beyond the distal end of the flexible elongate shaft across a predetermined proximal-distal distance range in association with an endoscopic procedure.

In a number of embodiments, the imaging endoscope assembly includes a collar element that surrounds at least portions of the imaging endoscope assembly's outer sleeve at a predetermined distance away from the distal end of the imaging endoscope. The collar element is configured for mating engagement with a receiver or receiving structure of the translation mechanism, such that longitudinal/surge displacement of the collar element across a given distance relative to the distal end of the flexible elongate shaft results in corresponding longitudinal/surge displacement of the distal end of the imaging endoscope.

As a result, in several embodiments the transport endoscope may have two robotic arms and corresponding end effectors carried thereby, as well as a flexible imaging endoscope, positioned in an environment beyond a distal end of a transport endoscope in accordance with an embodiment of the present disclosure.

In an embodiment, the flexible elongate assemblies comprising actuation assemblies and a flexible imaging endoscope assembly may be insertable to the plurality of channels within the flexible elongate shaft through the insertion inlets, with axes of the flexible elongate assemblies being parallel to the central axis of the flexible elongate shaft. Correspondingly or equivalently, each of the insertion inlets can have an insertion axis corresponding thereto, along which an actuation assembly or the flexible imaging endoscope assembly is insertable, such that the insertion axes of the insertion inlets are parallel to the central axis of the flexible elongate shaft at the proximal region or end of the flexible elongate shaft. For a given insertion inlet, a plane of an aperture or opening of the insertion inlet into and through which an actuation assembly or the flexible imaging endoscope assembly is insertable/inserted is transverse or perpendicular to its insertion axis.

When the actuation assemblies and the flexible imaging endoscope assembly have been fully inserted into the transport endoscope prior to their manipulation in an environment external to the distal end of the flexible elongate shaft during an endoscopic procedure, each collar element remains outside of and at least slightly away from the flexible elongate shaft, and in various embodiments outside of and at least slightly away from the transport endoscope's main body, such that longitudinal translation or surge motion of a given collar element across a predetermined proximal-distal distance range can freely occur by way of the translation unit, without interference from the flexible elongate shaft and/or main body.

Thus, the outer sleeve/coil of each actuation assembly must distally extend a sufficient length away from a distal border of its collar element such that the end effector reaches or approximately reaches the distal end of the flexible elongate shaft when the collar element resides at a most-proximal position relative to the translation unit. Similarly, the imaging endoscope assembly's outer sleeve must distally extend a sufficient length away from its collar element such that the distal end of the imaging endoscope resides at an intended position at, proximate to, or near the distal end of the flexible elongate shaft when the collar element is at a most-proximal position relative to the translation unit.

The main body may comprise a housing that extends to the proximal end, and a grip toward the distal end. Also, the main body may further comprise a strain relief boot which connects the main body and the flexible elongate shaft. In a more refined embodiment, the housing may include or be a cuboid or generally cuboid structure (e.g., a rectangular or generally rectangular cuboid tube), and a plurality of insertion inlets may be formed on an upper and/or top surface thereof toward the proximal end of the housing. Also, a joint member engages the transport endoscope with other elements of the slave system, e.g. the endoscope docking system or docking station, may be provided on a side surface of the housing. The grip provides a region, portion, or structure that a clinician (e.g., an endoscopist or surgeon) can hold to couple or engage the transport endoscope with other elements of the slave system, and spatially adjust, position, or move portions of the transport endoscope relative to other elements of the slave system and/or the subject or patient.

The following describes various Representative Embodiments and embodiments of improvements to the aforementioned flexible robotic endoscopy system.

Representative Embodiments of a Docking Block

FIGS. 1A-1D illustrate various view of the docking block 4 in an embodiment of the invention. The docking block 4 includes a longitudinal axis 12 and a lock pin recess 14. The docking block 4 is rectangular in shape and designed to be an interface between the endoscope and the flexible robotic endoscopy system, and is permanently attached to the proximal end of the control body 3 of the endoscope. The docking block 4 comprises of two or more instrument channel connectors/luers, an off-centered alignment position feature, and a lock-pin recess 14. The off-centered alignment position feature is disposed away from the geometrical center or centroid, or symmetrical axis, of the docking block 4. The lock-pin recess 14 provides a region or a receptacle for receiving a lock pin or a locking device to secure the docking block 4. The docking block 4 is used to aid or assist the endoscope to be aligned and connected with the docking mechanism.

Regarding the location of the docking block 4 on the control body 3 of the endoscope, it is necessary to consider the operability of endoscope during procedure (e.g. insertion of endoscope inside human body) and insertability of the surgical instrument into each lumen of the endoscope. Considering the operability of the endoscope, it is desirable to dispose or locate the docking block 4 on the endoscope control body 3 so that it does not disturb the operation of clinician. Considering the insertability of the surgical instrument into the endoscope lumen, it is desirable to make the instrument paths as straight as possible without introducing bending such as a Y-bend or S-bend at the instrument inlet 5 as it would damage the surgical instruments inside the lumens. To meet the above requirements, 1) the docking block 4 is disposed or located at a proximal end of the control body 3 of the endoscope; 2) the inlet of surgical instrument lumen is disposed or located at a proximal end of the docking block 4; and 3) the instrument lumen path in the docking block 4 is straight.

The docking block 4 is designed to allow the endoscope to be docked to the docking station or endoscope docking system. The docking block 4 encapsulates the surgical instrument inlets 5 and allows them to be exited from the top face of the docking block 4 through the channel connectors/ luers. The docking block 4 is attached to the proximal end of the endoscope control body 3. The attachment may be by temporary means, permanent means, or semi-permanent means. This configuration allows the endoscope to be docked to the docking mechanism of the docking station while it aligns the surgical instrument inlets 5 to the respective surgical instrument motorboxes, and the docking block 4 is attached to the endoscope body with mechanical durability and water tightness.

The docking block 4 is designed such that it can only be inserted into the docking station or endoscope docking system in two possible orientations—one correctly and another incorrectly. For instance, the docking block 4 can have a rectangular, generally rectangular, trapezoidal, or generally trapezoidal profile. With the off-centered alignment position feature on the rear side of the docking block 4, the endoscope can be inserted into the docking station in only one orientation. If a user or endoscopist attempts to insert the endoscope in another orientation, the user or endoscopist will experience a hindrance (due to the mating off-centered feature on the docking mechanism preventing the endoscope from being inserted further) after inserting the endoscope into the docking station at around 15 to 20 mm and cannot insert the endoscope further. This will trigger or alert the user to switch to another orientation for endoscope docking. Particularly, the user or endoscopist will need to switch the orientation of the endoscope by 180 degrees and insert the endoscope again.

Figure 1C:
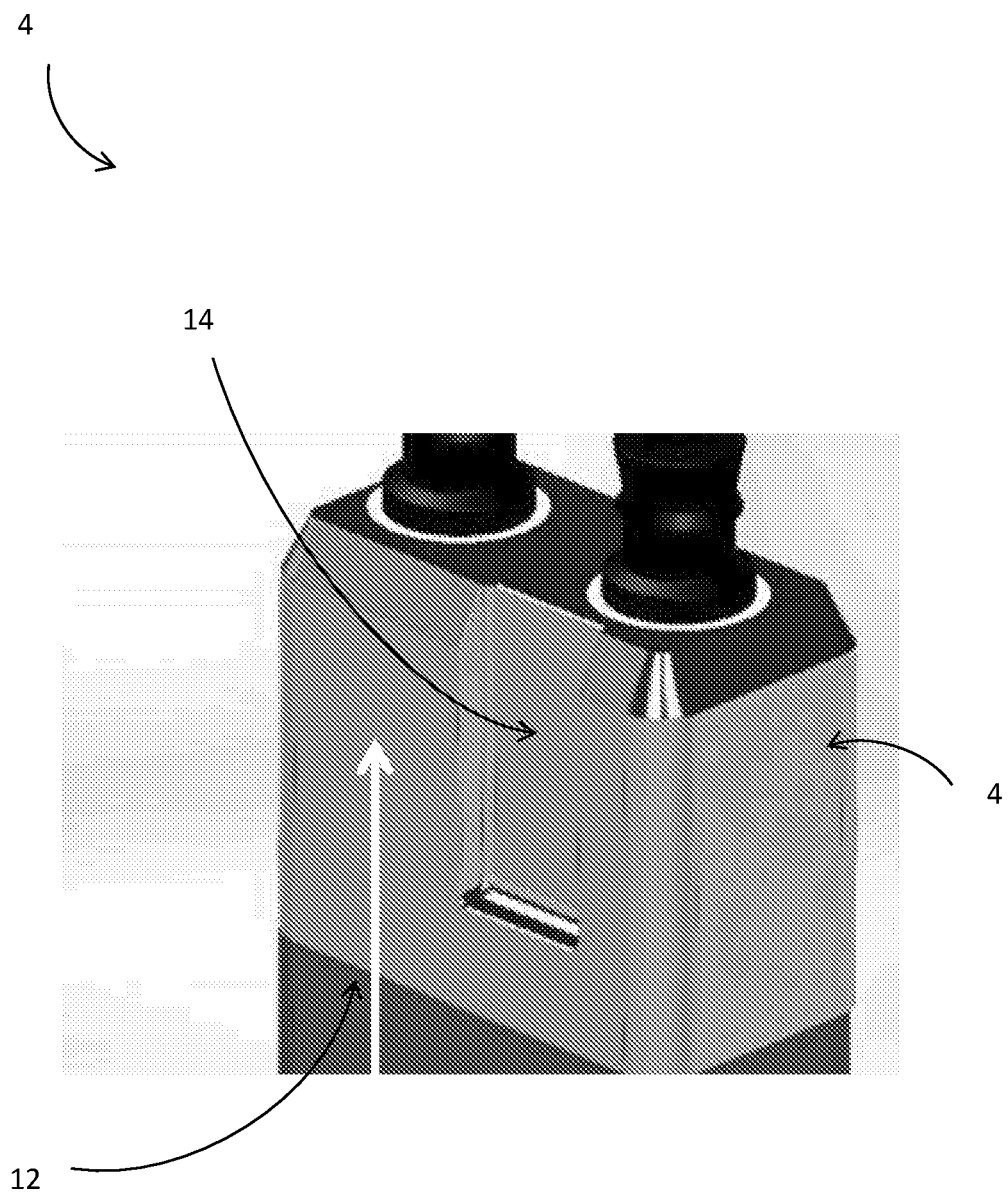
Figure 1D:
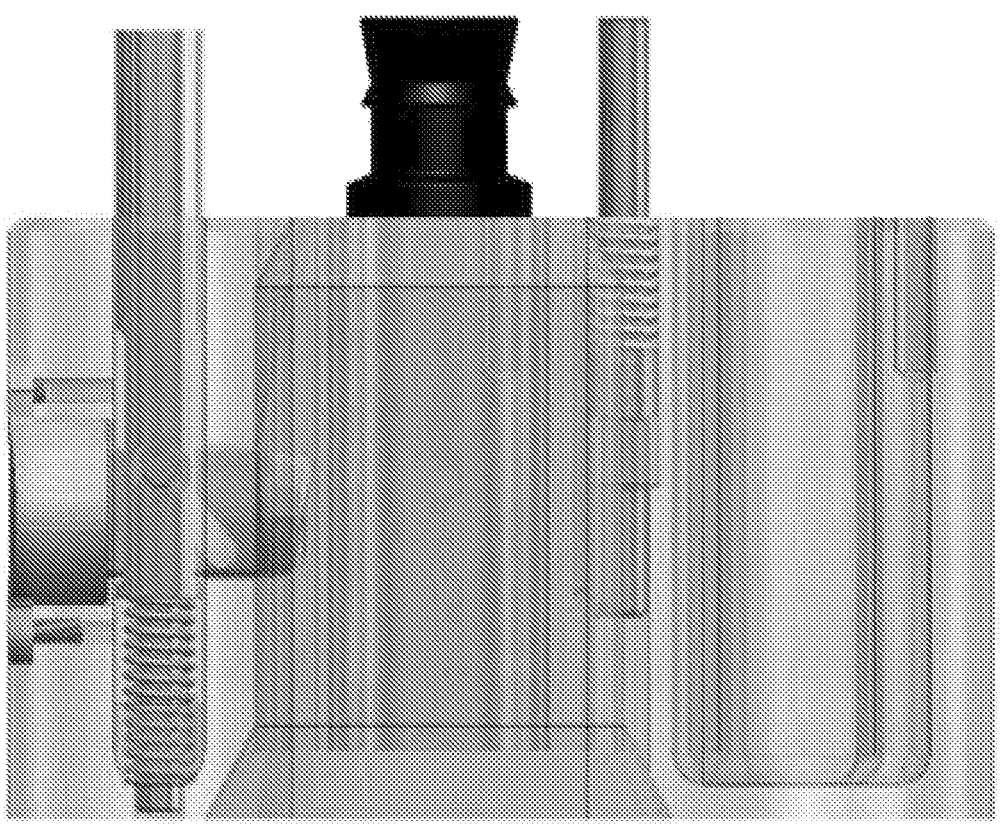

FIG. 1C show the off-centered alignment position feature and the lock-pin recess 14 on the docking block 4. The off-centered alignment position feature allows the docking connector to be inserted only in a pre-defined single orientation. The lock-pin recess 14 is a feature where a spring loaded pin of the same diameter as the recess is automatically inserted when the pin and the recess becomes axially aligned. The features of the off-centered alignment position and the lock-pin recess 14 are designed with generous fillets to allow a finger and a chemical-wipe/cloth to be used to assist in the endoscope cleaning process after an endoscopy procedure. Accordingly, the docking block 4 is easy to clean as there are no deep or concave features present on the exterior surfaces of the docking block 4. FIG. 1D shows a cut-away view of the docking block 4.

Representative Embodiments of Docking Station Brake Control

Various prior art references disclose the use of brakes and control of brakes in endoscopes or endoscope apparatus. U.S. Pat. No. 4,854,301 (Endoscope apparatus having a chair with a switch) discloses operation of an endoscope by attaching the endoscope to an arm which has an endoscope holder. An electro-magnetic brake is implemented on the arm, and switching on/off of the electro-magnetic brake is controlled by using a button which is implemented on the endoscope holder. U.S. Pat. No. 6,569,084 (Endoscope holder and endoscope device) discloses operation of an endoscope by attaching the endoscope to an arm which has an endoscope holder. The endoscope can be operated by using the controller which is implemented on the arm. An electro-magnetic brake is implemented on the arm, and switching on/off of the electro-magnetic brake is controlled by using a button which is implemented on the endoscope holder. JP 4402444 (Endoscope holder and endoscope device) discloses operation of an endoscope by attaching the endoscope control body 3 to the arm which has an endoscope holder and holding the endoscope insertion portion by the holder which is implemented on another arm. An electro-magnetic brake is implemented on an arm, and switching on/off of the electro-magnetic brake is controlled by using a button which is implemented on the endoscope holder.

A technical problem associated with the aforementioned prior art references is that an endoscopist is not able to operate the brake control button/switch which is implemented on arm or endoscope holder by using his left hand, while operating the endoscope which is attached to endoscope holder. When the endoscopist operates the endoscope which is attached to endoscope holder, the endoscopist has to release his left hand, which is holding endoscope control body 3, from the endoscope control body 3. Alternatively, the endoscopist has to operate the brake control by using his right hand, which is holding endoscope insertion part.

It is thus an objective to improve operability of brake control to improve efficiency of endoscopic treatment. The endoscopist would be enabled to operate the brake control, while holding the endoscope control body 3 by his left hand. The endoscopist would also be enabled to hold the endoscope control body 3 and insertion portion by his hand, while controlling the brake.

A possible solution is to implement a brake control button or switch or sensor on the endoscope control body 3. There are various conditions for implementation of the brake control button/switch/sensor. The location of brake control button/switch/sensor is where an endoscopist can control by using his left hand, or where an endoscopist can control the button/switch/sensor when he is gripping endoscope control body 3 by his left hand. The working conditions of the brake are as follows:

(a) While the button is being pressed by the endoscopist's left hand finger or the sensor detects that the endoscopist is gripping the control body 3 by his left hand, the brake is off Thus, the endoscopist can continue pushing the button or working on the sensor.

(b) Once the button is pressed or the switch is turned on, brake control can be changed, ON<->OFF. The endoscopist can easily push button/switch or work on sensor.

When the endoscopist does not intend to operate button/ switch/sensor, the button/switch/sensor does not function. The endoscope is electrically connected to the system (PSC Main Processor/SCU Main Processor) which controls the brake control.

Further to working condition (a) above, there are various embodiments of the button/switch/sensor while it is being pressed and the brake is off, as described hereinafter.

Figure 2A:
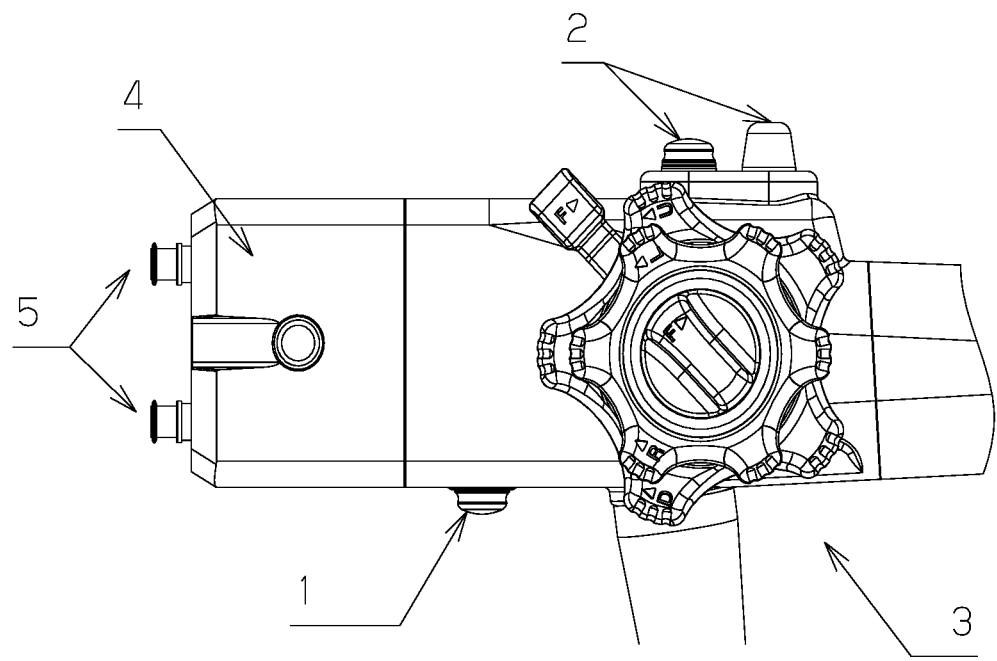
FIGS. 2A-2C are illustrations relating to docking station brake control for the endoscopy system, in accordance with an embodiment of the present disclosure.
Figure 2B:
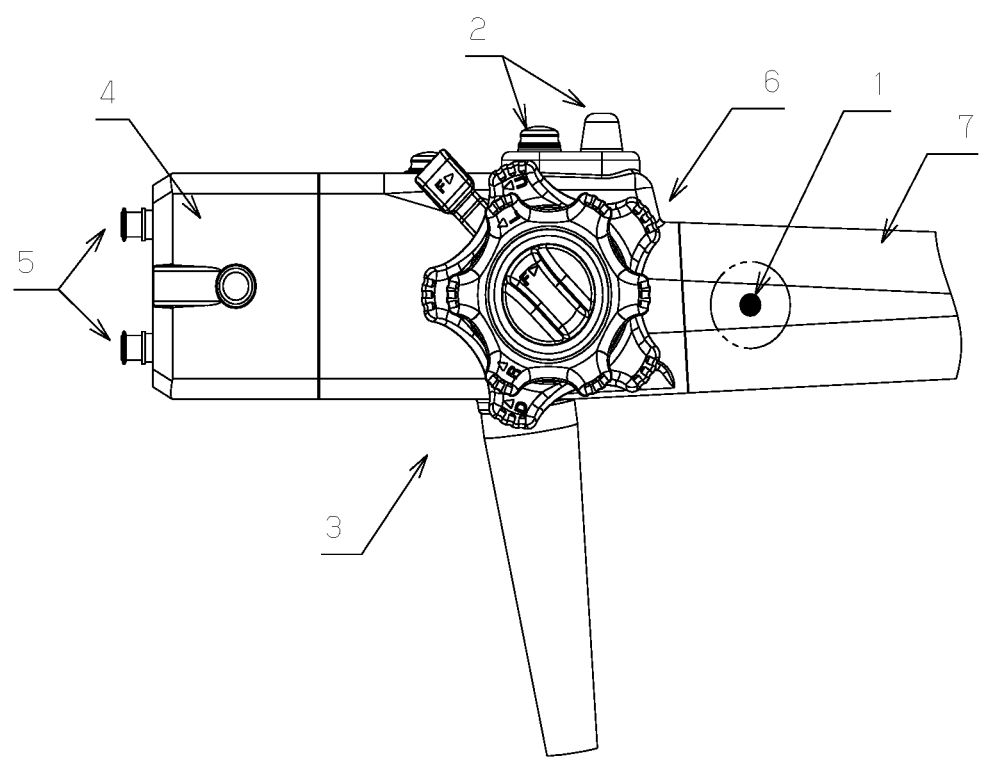
Figure 2C:
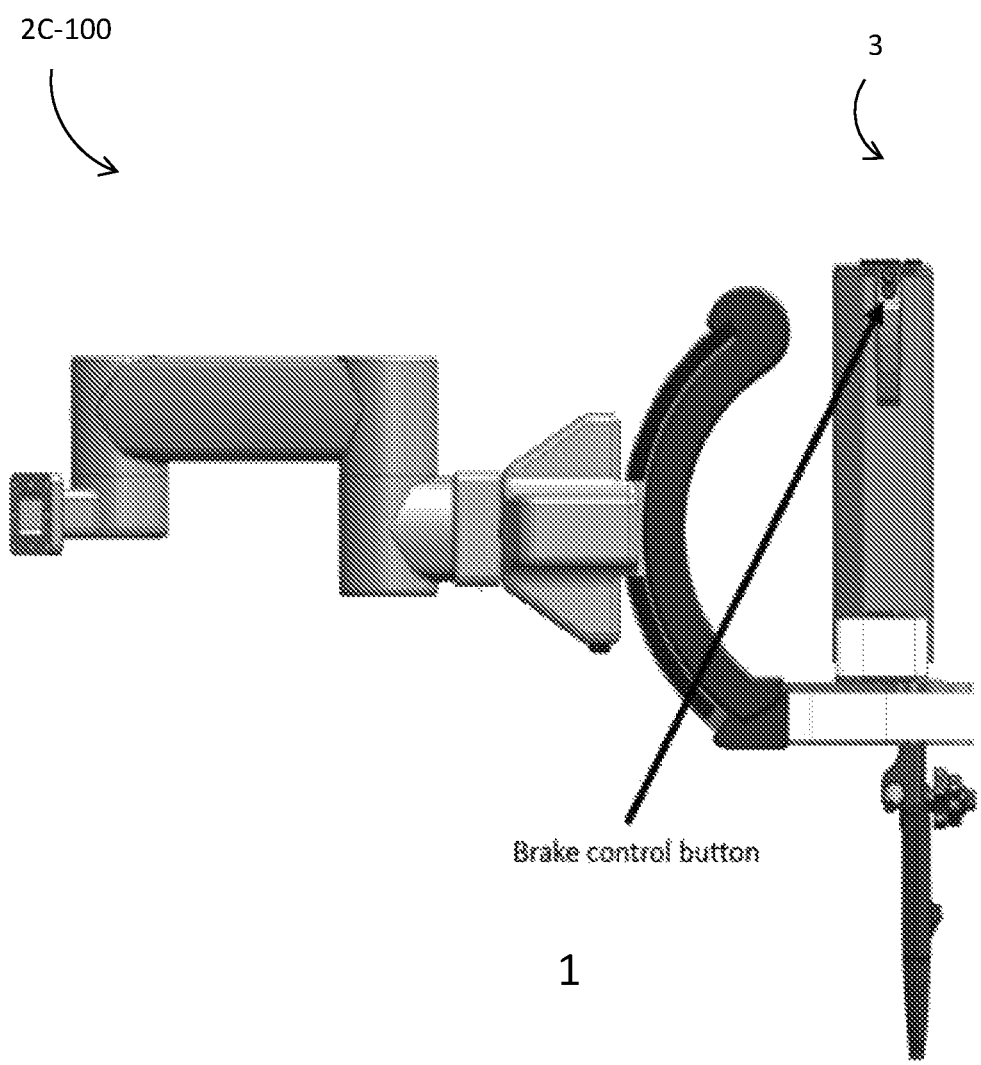

FIGS. 2A-2C illustrate embodiments using a brake control function 1 located on the endoscope control body 3, gas and water feeding and suction buttons 2, the docking block 4 and instrument inlets 5. The supplementations or components of these embodiments include:

a remote control button as with commercial endoscopes; and implementation of the button on the control body 3, where the finger of the endoscopist can access. FIG. 2C illustrates the brake control function 1 in place 2C-100 on the Docking Station.

The embodiments can use a lever-type switch, e.g. lever button or push lever. The supplementations or components of these embodiments include a lever-type switch is implemented at the step of control body 3 and used like a gun trigger. When the lever switch is turned on, the middle finger of the endoscopist is used for pushing the switch. The switch may include a spring-back feature—for brake off, the endoscopist continues to push the lever; and for brake on, the endoscopist releases the lever.

The embodiments can include a knob-type switch, e.g. a rotatable lever button. The supplementations or components of these embodiments include an additional knob, such as a rotation lever, that is implemented with angulation control knobs 6. The additional knob is operated by using a left hand thumb of the endoscopist. The switch may include a spring-back feature—for brake off, the endoscopist rotates the knob from initial position to a specified angulation position and stop the knob at this position; and for brake on, the endoscopist releases the knob. Alternatively, the switch does not include the spring-back feature—for brake off, the endoscopist rotates the knob from initial position to a specified angulation position (the endoscopist can release his thumb from the knob); and for brake on, the endoscopist rotates the knob back to the initial position. Examples of implementing such a switch/sensor include using mechanical button switch which is implemented inside the control body 3 and functioned by a rotating knob. Another example is the use of angulation sensors.

FIG. 2B illustrates embodiments using a brake control function 1 (which can be a button or sensor) located on the left or right side of the control body 3 grip. The sensors sense whether the endoscopist is holding the control body 3 grip. The sensor/button is implemented on either right or left side of the control body 3 grip. For the right side, the endoscopist uses his fingers for working the sensor or pushing the button. For the left side, the endoscopist uses his palm for working the sensor or pushing the button. Examples of such a button/switch/sensor include mechanical button, light sensor, touch sensor, temperature sensor, and pressure sensor.

Further to working condition (b) above, there are various embodiments of the button/switch/sensor once it is pressed or turned on, so that the brake can be changed between on and off, as described hereinafter.

In embodiments using a push button as illustrated in FIG. 2A, the button is the remote control button as with commercial endoscopes, and the button is implemented on the control body 3, where the finger of the endoscopist can access. In other embodiments, the button is the remote control button as with commercial endoscopes In embodiments using a lever-type switch, a lever-type switch is implemented at the step of control body 3 and used like a gun trigger. When the lever switch is turned on, the middle finger of the endoscopist is used for pushing the switch. The switch may include a spring-back feature. To turn off the brake, the endoscopist pushes the lever (he can release his finger from the lever). To turn on the brake, the endoscopist pushes the lever, again (he can release his finger from the lever).

In embodiments using a knob-type switch, an additional knob, e.g. a rotation lever, is implemented with angulation control knobs 6 in FIG. 2B. The additional knob is operated by using a left hand thumb of the endoscopist. The switch may include a spring-back feature. To turn off the brake, the endoscopist rotates the knob from initial position to a specified angulation position (he can release his finger from the knob). To turn on the brake, the endoscopist rotates the knob from initial position to a specified angulation position, again (he can release his finger from the knob). Examples of such a brake control function include a switch which is implemented inside the control body 3 and functioned by a rotating knob, as well as angulation sensors.

In other embodiments, sensors can be used for detecting signals from the endoscopist directly, whereby such sensors are implemented in the system. The endoscopist does not have to use both hands and all fingers. An example of such brake control function 1 is a voice sensor.

Figure 4A:
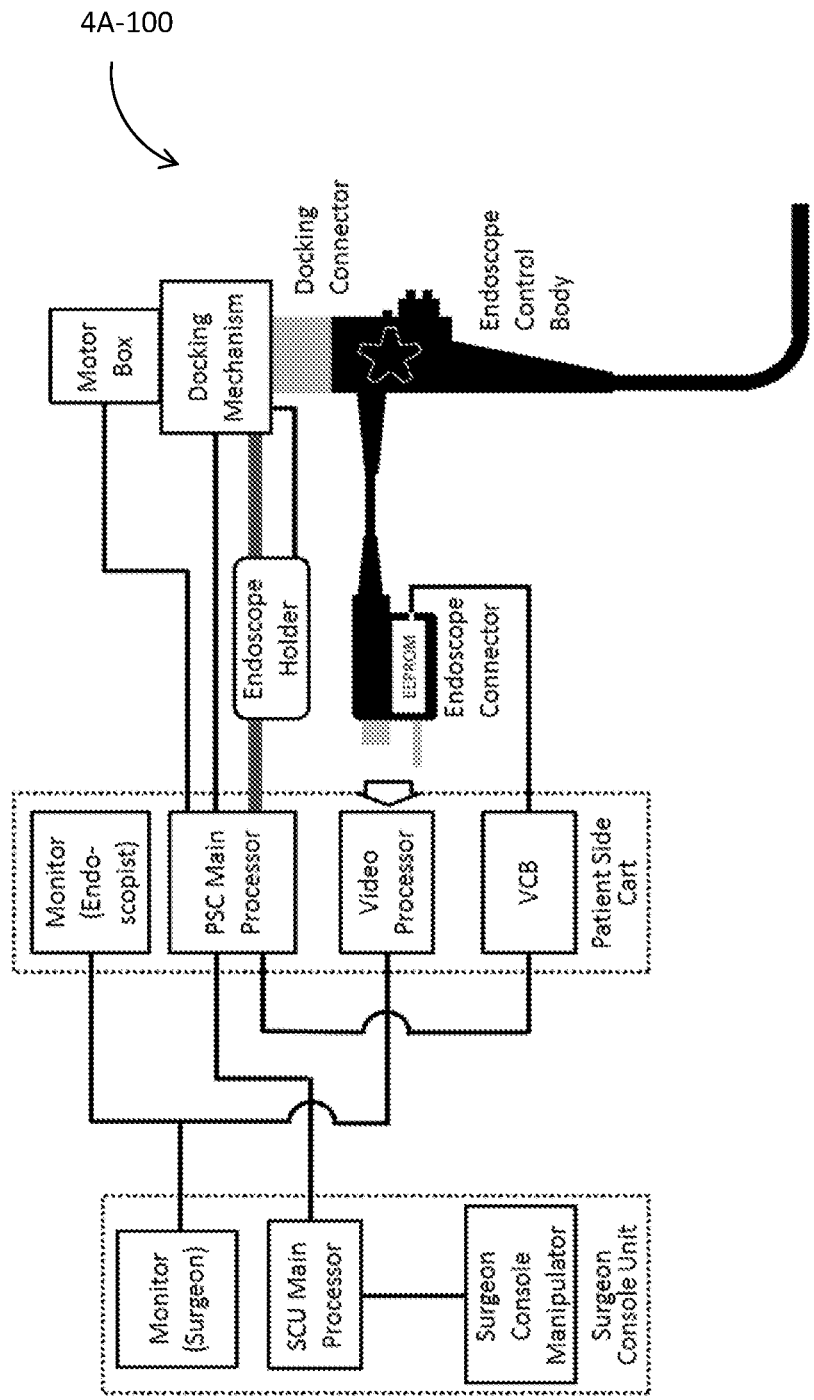
FIGS. 4A-4B are illustrations relating to a memory chip for the endoscopy system, in accordance with an embodiment of the present disclosure.

FIG. 4A shows a block diagram of a system implementing the docking station brake control. The brake control for the docking station or endoscope docking system provides an additional safety function, particularly the prevention of unintended working of brake ON/OFF. The safety button/switch/sensor can be implemented; and the button/switch/sensor for each function can be combined for safety function. It is to be desired that the endoscopist can confirm brake ON/OFF visually during endoscopy procedure. For example, brake condition ON/OFF can be indicated on a main monitor, sub-monitor, and/or dedicated indication equipment. Another safety function of the docking station brake control is for prevention of operation confusion between surgeon and endoscopist during procedure. Specifically, it does not enable endoscopist to turn off the brake, while a surgeon is operating robotic instruments at the console or surgeon console unit (SCU).

An advantageous effect of the docking station brake control is an improvement of efficiency of endoscopic treatment, as a result of improvement in operability. The endoscopist can easily operate the brake control, holding the endoscope control body by his left hand. The endoscopist can hold the endoscope control body and insertion portion by his hand, when he is also controlling the brake.

Representative Embodiments of Wire Tension Adjustment and/or Relaxation

In endoscopic submucosal dissection (ESD) procedure protocol, the endoscope is first inserted into the patient's gastrointestinal (GI) tract to reach the target site. The surgical instruments are next inserted into the endoscope lumens. These steps are similar to conventional ESD procedures. It is easier for the clinicians or endoscopists to insert the endoscope alone, because once the surgical instruments are inserted into the endoscope, the endoscope becomes stiffer and more torque is required for the user to rotate the control knobs of the endoscope. The endoscope is further stiffened when proper tension is applied to the tendons of the surgical instruments. If more torque is needed to control the knobs, the endoscope control wires may get damaged and wear out more quickly due to the higher tension applied.

With the current surgical instrument design in which tendon tension is not preset in the surgical instrument adapter, tension can be applied and relaxed using actuators in the motorbox. Automatic pre-tensioning algorithms take advantage of this design to apply optimal tension depending on tortuosity of the surgical instruments. A similar technique could be used to change the tendon tension before adjustment of the control knobs of the endoscope. This could potentially reduce damage to the control wires of the endoscope and make it easier for the user to change bending angulation of the endoscope distal end.

To fully or partially relax the tendon tension of the surgical instruments, there may be a button on the endoscope or the endoscope docking system/docking station where the endoscope is docked. After adjustment of the endoscope bending angulation, this button could be used again to retention the surgical instruments. Depending on change of the angulation, the same tension could be applied. Alternatively, a new optimal tension could be applied for the new path using the automatic pre-tensioning algorithms. This sequence can be done without detaching the surgical instrument adapter from the motorbox.

Tension release can be done automatically if there is a sensor such as encoders for angulation control knobs 6 of the endoscope. As soon as the control knobs are rotated by the user or endoscopist, signals from the sensors are transmitted and processed by the PSC Main Processor and it detects motion of the endoscope bending section. Tension of the surgical instruments is subsequently fully or partially released. If any information of the endoscope such as the bending angulation of the endoscope, total tortuosity of the endoscope in the path, among others, is available and can be transferred from the endoscope to the system, this knowledge could be used to partially adjust the tendon tension rather than to fully relax the tension.

Various prior art references disclose the relaxing or relaxation of wires or wire tension. WO 2014/123019 A1 discloses a bending apparatus. Japanese Unexamined Patent Application Publication No. 2013-172905 discloses an optical rotary encoder or liner encoder on moving parts. U.S. Pat. No. 7,828,725 B2 discloses a bent state holding mechanism of an endoscope, as well as an angulation lock mechanism of conventional endoscopes. WO 2013/136583 A1 discloses an operation control device for insertion apparatus, wherein movement of joints which are in the endoscope channels is restricted.

A technical problem associated with the aforementioned prior art references is that the endoscope lumens and/or robotic instruments may get damaged if the endoscope is operated while robotic instrument wires are tensioned. The robotic instruments may injure patient's body cavity if the endoscope is operated while the instrument wires are tensioned. Although the prior art WO 2013/136583 A1 discloses prevention of the endoscope and the instruments from being damaged, it does not take into account operating the endoscope during surgery.

It is thus an objective to relax the robotic instrument wires while an endoscopist is operating the endoscope.

Figure 3A:
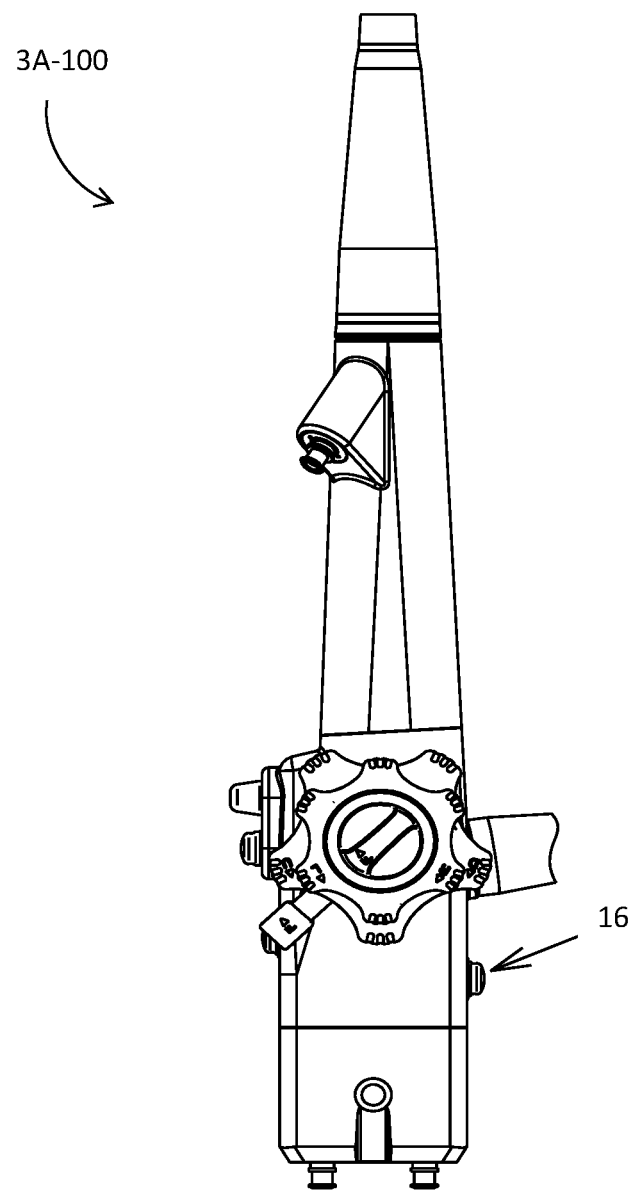
FIGS. 3A-3E are illustrations relating to wire tension adjustment and/or relaxation for the endoscopy system, in accordance with an embodiment of the present disclosure.
Figure 3B:
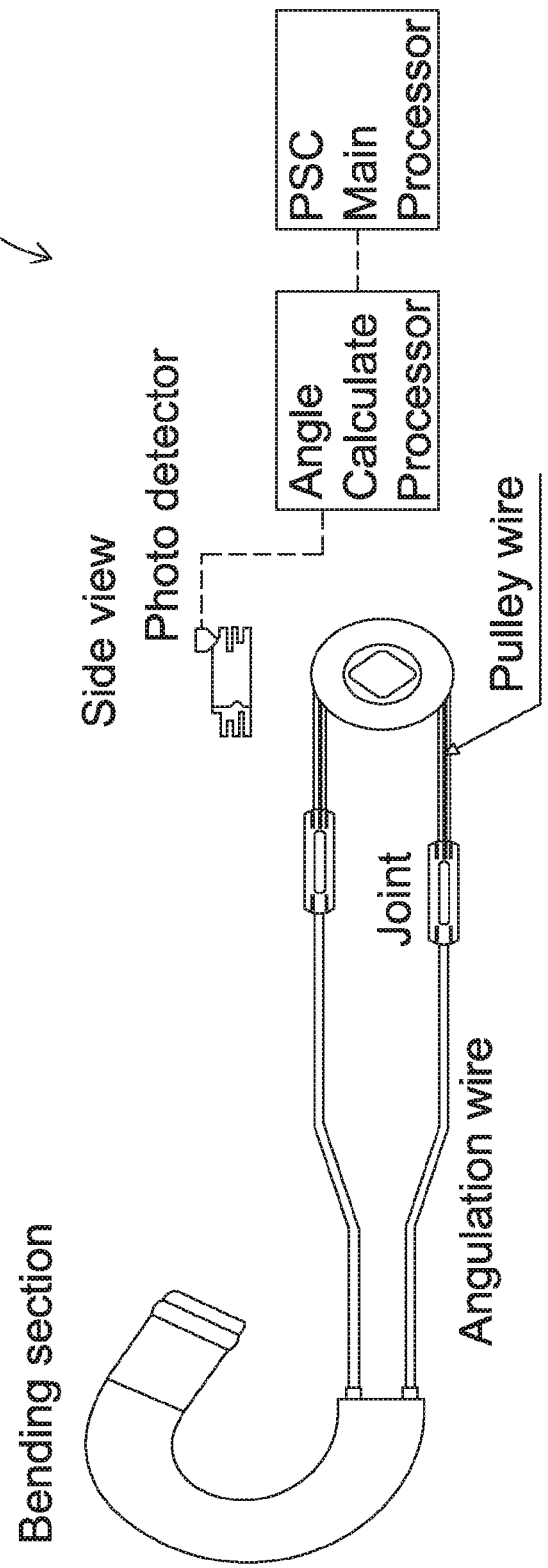
Figure 3C:
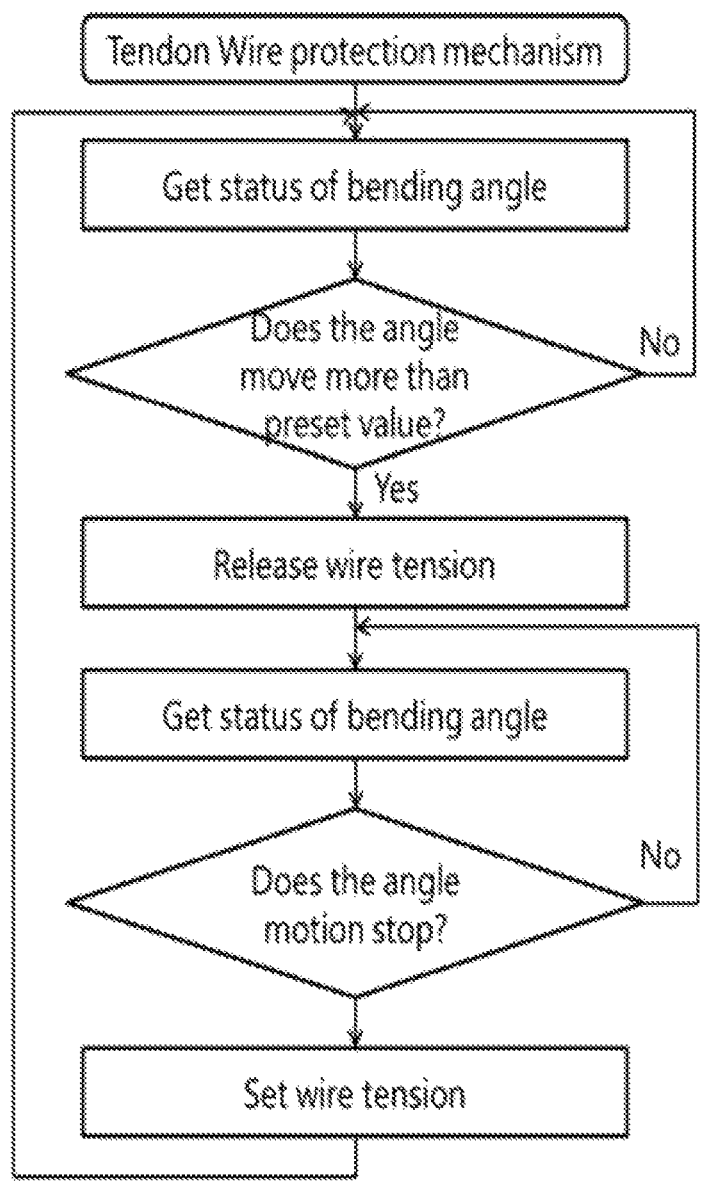
Figure 3D:
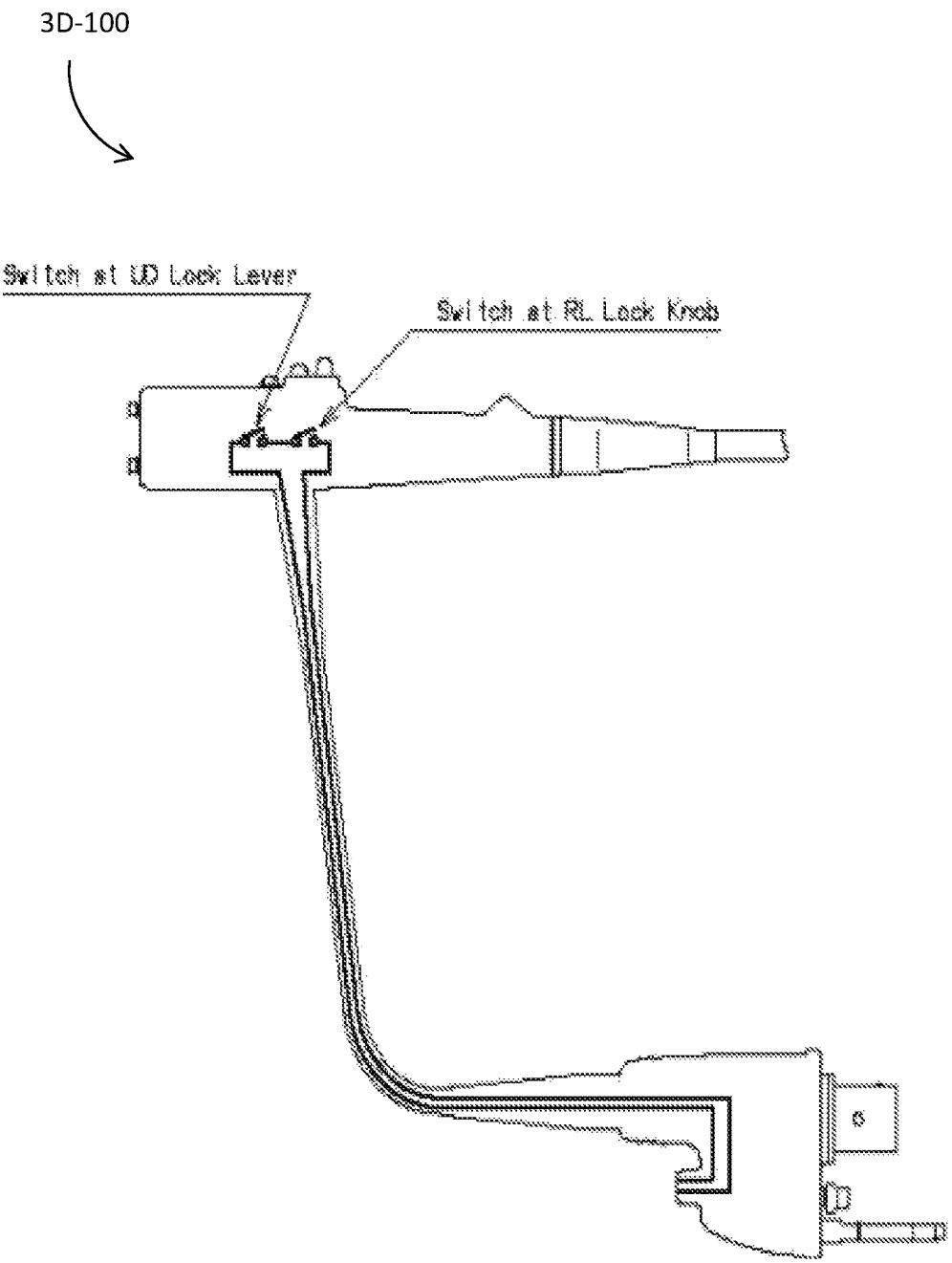
Figure 3E:
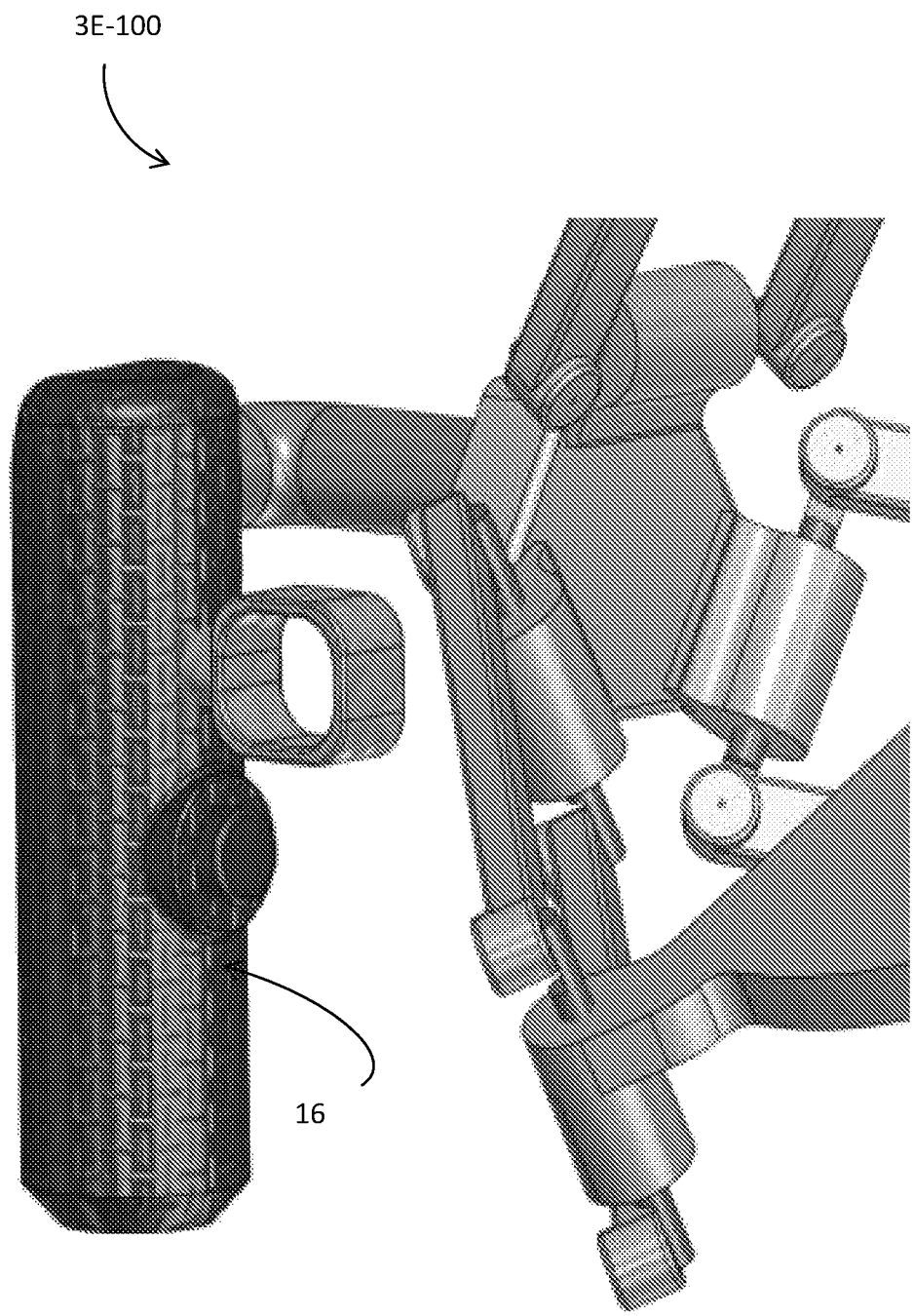

One solution A would be to allow the endoscopist and/or a surgeon to switch on or off the instrument wire tension. A tension control function 16 can be implemented or used on the control body 3 of the endoscope or on the controller at the surgeon console unit. FIG. 3A illustrates embodiments of an implementation of solution A 3A-100. A tension control function 16 is placed to switch the wire tension on the endoscope control body 3 or the controller at the surgeon console unit. The position of the A tension control function 16 can be similar to remote control buttons of conventional endoscopes. In this configuration, a user or an endoscopist can change the situation of the instrument wires (relax or taut) consciously by pressing the button. FIG. 3B illustrates a wire configuration 3B-100 and FIG. 3C shows a flowchart 3C-100 for the tension control. FIG. 3D illustrates the wire configuration 3D-100 in the endoscope system. FIG. 3E illustrates the tension control function 16 in an alternate location at a surgeon console unit 3E-100.

One solution B would be to automatically relax wire tension of robotic arms by detecting angulation operation. A rotary encoder can be used to sense the rotation motion of a pulley in the control body 3. Alternatively or additionally, a linear encoder can be used to sense the movement of angulation wires in the control body 3. An embodiments of an implementation of solution B with linear encoders has joints in the control body 3 which connects angulation wires for each bending directions and pulley wires. Wires and encoders can be used for Up and Down angulation. On a lateral side of the joint, a pattern to be detected by the sensor is located. The pattern is read or sensed using the sensor placed on the side of the joint. At least one linear encoder is required to detect the movement of Up and Down endoscope bending, and using two encoders reduces the effect of backlash.

FIG. 3B illustrates embodiments of an implementation of solution B 3B-100 with rotary encoders. A pattern on the surface or lateral wall of the pulley is read or sensed. If location information is needed, initialization on the reference position as the bending section is straightened is performed before operating the endoscope. Otherwise, the reference position sensor is placed separately. Either optical or magnetic encoders can be used. Absolute type encoders may also be used.

One solution C would be to use a shape or motion detection method to detect the movement of the endoscope bending section. Magnetometric sensors such as those in colon navigation systems which display the shape of an endoscope insertion part during an operation can be used; optical fibers can be used to sense the shape of the bending section; and/or an accelerometer can be used in the distal end of the endoscope. There are two ways to detect the bending movement by using the magnetometric sensors. One of them is to place at least two antennas through the distal end to the proximal end of the bending section, and preferably one antenna is placed at the distal end and the other is at the proximal end of the bending section. Antennas catch magnetic intensity from the magnetic field generator which is located at the patient side. Thereafter, the bending motion can be detected from the relative position of the two antennas. If the endoscope has more antennas in the bending section, the bending angle can be estimated. The other way of the detection with magnetometry is to place at least two coils in the bending section, and the magnetic intensity from the coils is detected by a receiver at the patient side. At least one optical fiber sensor is used in the bending section; and at least one accelerometer is used at the distal end or in the bending section to detect distal end motion.

FIG. 3C illustrates a flowchart 3C-100 detailing the steps to change the wire condition between relaxed and taut (for solutions B and C).

One solution D would be to use the docking station brake control switch as an instrument wire tension switch. When the brake of the endoscope holder on the docking station becomes OFF to operate the endoscope, the arms become relaxed and are pulled back into the channel. The docking station has a button to unlock the brake of the endoscope holder as illustrated in FIG. 2C. The unlock button can be also on the control body 3 of the endoscope, or a foot pedal. When the brake is unlocked, the instrument wire tension is automatically relaxed, and it is pulled back into the endoscope channel Using the robotic arms when the brake is unlocked is dangerous to patients. In case of emergency such as bleeding and perforation, the endoscope needs to be operated immediately. Therefore, such an automatic process saves complex steps for users/endoscopists.

One solution E would use the endoscope's angulation lock as an instrument wire tension switch. When either Up/Down or Right/Left angulation is unlocked, the arms become relaxed and pulled back into the channel FIG. 3D shows embodiments of an implementation of solution E. Switches are added to the Up/Down angulation lock lever and the Right/Left angulation lock knob. The two switches are connected in series. When either the Up/Down or the Right/Left angulation is unlocked, the instrument wire tension is automatically relaxed, and it is pulled back into the endoscope channel. In order to use the robotic instruments, both endoscope angulations need to be locked for safety (see the table below). Similar to solution D, this reduces steps which need to be done in case of emergency.

TABLE 1

Instrument wire tension and angulation lock

| | | Right/Left Angulation | |
|---|---|---|---|
| | | Lock | Free |
| Up/Down Angulation | Lock | Taut (pre-tension) | Relaxed |
| | Free | Relaxed | Relaxed |

For each of solutions A to E, the instrument wire condition (i.e. the robotic instruments are ready for use or not) is indicated on a main screen, sub-screen, and/or dedicated indication equipment. Users cannot apply high frequency electricity to a robotic cautery device during the wires are relaxed. The solutions A to E can be used together in any combination. For example, using the angulation detection (solution B) can be combined with the switch for users (solution A) to improve safety against misuses.

There are several advantageous effects in implementing the above solutions, listed as follows:

Prevent the endoscope from being damaged.

Prevent the instruments from being damaged.

Reduce a risk of damaging patient's body by a protruded instrument during endoscope operation.

Reduce operation time because the instruments do not need to be manually withdrawn from the endoscope in order to operate the endoscope during a surgery.

Since wire tension of the instrument is indicated on the screen, an endoscopist and a surgeon can understand each other's operation easily.

It is safer because the high frequency current does not flow unintentionally through the cautery device to a patient's body while an endoscopist is operating the endoscope.

Representative Embodiments of Surgical Instrument Damage Protection through Bending Angle Sensing The sensing of the bending angle of the endoscope can be used to protect the surgical instruments from being damaged inside the endoscope. A bending radius of the endoscope bending section is highly related to usability of the endoscope insertion. Generally speaking, the smaller the bending radius is, the easier for the clinicians to insert the endoscope into the patient's body. This design parameter is limited by other design factors such as the endoscope outer diameter, the number of lumens inside the endoscope, among others. The surgical instruments are ideally designed to pass through any tortuous paths inside the endoscope lumens. However, to minimize the endoscope outer diameter, the lumens are required to be kept smaller. This makes it challenging for the surgical instruments to go through a larger bending angulation with a small bending radius on the distal end of the endoscope. If the surgical instrument cannot be inserted without damaging itself or the endoscope, there should be a warning sign displayed to the user or mechanism to avoid forcible insertion and prevent the user from inserting the surgical instruments further into the endoscope lumens. The endoscope can have a sensing mechanism or sensors inside to measure the bending angle of the endoscope tip or distal end. Alternatively, sensors can be placed at other locations of the endoscope, e.g. at the proximal end to get an estimated gauge, as readily understood by the skilled person. The sensors include, but are not limited to, electromagnetic sensors, optical fibers, X-rays, and ultrasound. Another approach is to estimate the bending angle from tension applied to the control wires, position sensed at the control knobs of the endoscope, among others.

When the bending angle of the bending section exceeds the maximum bending angle at which the surgical instrument can be inserted, a warning sign can be displayed on the system to urge the user not to keep pushing the surgical instrument along the bending section, or to relax the bending angulation to push the surgical instrument further without damaging the endoscope and/or itself. An actuation mechanism can be used to block the surgical instrument from being pushed into the endoscope if the bending angle is too big. This mechanism can be designed inside the endoscope.

Representative Embodiments of a Memory Chip in Endoscope

Regarding a GI endoscope, there are some predefined, predetermined, or known types of insertion portion length in accordance with the GI tract (upper GI or lower GI). To focus on same type insertion portion length GI endoscope, there are some tolerances about each portion because of part tolerances and manufacturing tolerances assembled in the endoscope.

When ESD is performed by using manual ESD devices, clinicians use different length devices for each endoscope insertion portion length or use special tools to adjust device position forward or backward to make ESD procedure more efficient (as disclosed in WO 2013/065509). When ESD procedure is performed by using robotic ESD devices controlled by a controller, clinicians need to adjust device position forward or backward, too (as disclosed in WO 2015/012163). For both arts, it is common that the hands of clinicians or assistants are used for adjustment of the device position in the endoscope lumen.

In consideration when ESD is performed by robotic instrument inserted into endoscope and controlled remotely, e.g. master and slave systems, performance of robotic instrument would not be sufficient to perform ESD procedure, when the length of robotic instrument is not suitable for the length of endoscope lumen. In consideration of using master and salve control to operate robotic instruments remotely, the instruments need to be translated forward or backward by the motor on the translation stage to adjust instrument position in endoscope lumen for efficient ESD procedure. When the instrument length is shorter than endoscope lumen, the end effector of the instrument cannot access the ESD target inside body. When the instrument length is longer than endoscope lumen, the end effector of the instrument cannot be positioned at the initial position in the endoscope lumen for efficient ESD. It is difficult for the operator to observe the ESD procedure via imaging sensor which is implemented at the distal end of the endoscope, because the distance from the distal end to the ESD target lesion is too far to perform ESD.

In case when the length of instrument shaft is much longer than the length of endoscope lumen and the space to translate instruments to optimum position is long enough (e.g. the stroke of the motor on translation stage), the size of the system is increased, especially the translation stage: It is necessary to make enough space on the translation stage to translate each instrument to the optimum position. Further, the whole system has increased complication. It is necessary to implement position sensors into either/both distal end of endoscope and/or instruments to adjust the position of instruments by using a remote controller.

Considering the aforementioned, when the robotic instruments are operated via endoscope lumen by the master and slave system, the position of instruments in endoscope lumen is important make ESD procedure efficient.

Regarding robotic instruments controlled by the master and slave system, robotic instruments which are inserted into the endoscope lumen can be translated forward and backward, as instruments have attached motors which are implemented on the docking station. One of the technical problems is that the robotic instruments which are being inserted into endoscope lumens cannot be translated to the optimum position for ESD procedure by using robotic instruments, considering the tolerances of the length of the endoscope lumens. The first concern is the increasing size of the translation stage as it is necessary to make enough space on the translation stage to translate each instrument to the optimum position. The second concern is the complication of the system configuration as it is necessary to implement position sensors into either/both distal end of endoscope and/or instruments to translate each instrument to the optimum position. Another technical problem is the inability to prevent misuse of instruments whose insertion shaft length is different for different GI tract (upper GI or lower GI) (there are some types of instruments whose insertion shaft portion is different for different GI tract).

It is thus an objective to enable the robotic instrument to be translated to the optimum position (initial position) in the endoscope lumen for each endoscope with a different lumen length.

One possible solution would be to implement a memory chip in the endoscope. More particularly, an Electrically Erasable Programmable Read-Only Memory (EEPROM) can be implemented in available space inside the endoscope. The data written in EEPROM can be read by the system (PSC Main Processor and/or SCU Main Processor). Data of the endoscope lumen length measured at manufacturing process is written in EEPROM of endoscope. The system (PSC Main Processor and/or SCU Main Processor) reads the data to recognize the instrument length used in ESD procedure previously. The robotic instruments on the translation stage are automatically translated to the optimum position for ESD procedure according to endoscope lumen length and instrument length. The endoscope is electrically connected to the system which controls the position of instruments.

Figure 4B:
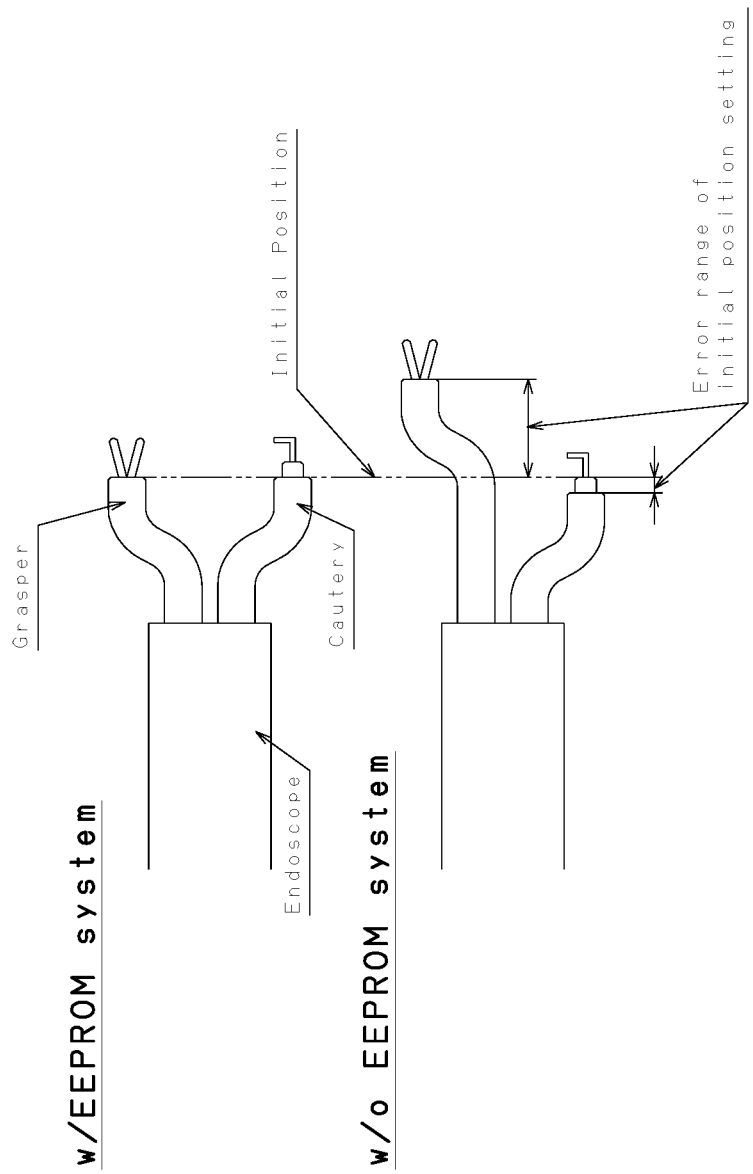

A specially-designed endoscope is part of the system. Exchanging and sharing information between the main processor(s) and the endoscope can be useful. The data can be sent between the endoscope and the PSC Main Processor or another device to read and/or write data on the chip in the endoscope. They can be transmitted through data cables or wirelessly. In FIG. 4A, the endoscope is electrically and indirectly (via other system; e.g. a valve controller box as described later) connected 4A-100 to the PSC Main Processor. FIG. 4B illustrates a comparison 4B-100 between an endoscope system with EEPROM and without EEPROM to illustrate an example of positional error during surgical instrument initialization.

In implementation, the system (PSC Main Processor and/or SCU Main Processor) to remote-control instruments reads the data of the endoscope lumen length from EEPROM in the endoscope. The data stored on the chip can be used to check if the combination of the endoscope and surgical instruments installed is correct. Depending on the type of procedures, where to insert the endoscope, and/or clinician preference, the working length of the endoscope may change. For example, upper GI endoscopes are typically shorter than lower GI ones. There are a few working lengths of the endoscopes available even for lower GI. If the surgical instruments are designed to be dependent on the total length of the endoscope, the system needs to tell the user if the surgical instruments installed to the system are correct. If the surgical instrument is shorter, its tip may not come out from the endoscope distal end.

The adjustment of instrument initial position for ESD procedure is in accordance with the data of the endoscope lumen length written in EEPROM. The tolerances of the total length of the endoscope that affect initialization of the surgical instruments can be accommodated. Currently, there are some tolerances about each portion because of part tolerances and manufacturing tolerances assembled in the endoscope. The stack-up tolerances of the total length of the endoscope may affect intuitive teleoperation control of the surgical instruments because their position of the end effectors are estimated well from the proximal end of the surgical instruments through sensors such as motor encoders. Therefore, knowing the total length of the endoscope mitigates this problem.

The system (PSC Main Processor and/or SCU Main Processor) connected to endoscope can recognize the serial number and model name of the endoscope. The system (PSC Main Processor and/or SCU Main Processor) to remote-control instruments writes the additional data about clinical histories from its system to EEPROM in the endoscope. The clinical histories include history of instruments inserted into the endoscope (based on serial/manufacturing numbers); history of usage count of instruments inserted into the endoscope; history of usage count of the endoscope connected to the docking station; and information of the facility that the system is used in (e.g. facility name, cleaning machine (washer-disinfector, automated endoscope reprocessor, detergent, disinfectant, and/or sterilant).

The data can be also stored on the chip in the endoscope and transferred to the PSC Main Processor to tune control parameters of the surgical instruments, if any calibration data of the endoscope that may enhance performance of the surgical instruments is available. For example, if friction of the endoscope lumens is measured and stored on the chip in advance, the data can be transferred to the system to adjust translational force of the surgical instruments to accommodate the friction.

The data and parameters stored in the memory chip or EEPROM can be ported or migrated to another endoscope in the event the endoscope wherein the EEPROM currently resides is damaged. Data analysis can also be performed, including on logs of errors, data logs of reparations, cleaning jobs, types of instruments, usability of instruments (e.g. with regard to dimensions), calibration data, and accommodation of frictional forces on instruments which affect the motor output for moving the instruments.

It is possible to restrict the operation of instrument at the surgeon console unit, when the data of EEPROM of endoscope is not read by the system. Instruments cannot be operated at the surgeon console unit when the endoscope is not connected to PSC Main Processor or valve controller box.

In a parent-child endoscope, implementation of EEPROM can be used therein to translate child endoscope to the optimum position. EEPROMs are implemented into both parent and child scopes. The system (PSC Main Processor and/or SCU Main Processor) reads the data of parent endoscope lumen length and child endoscope insertion tube length from both EEPROMs, and can translate the child endoscope to the optimum position for parent endoscope at the start of ESD procedure (initial position).

There are several advantageous effects in implementing a memory chip or EEPROM in the endoscope, listed as follows:

- Enable the robotic instrument to be translated easily to the optimum position (initial position) in the endoscope lumen for each endoscope with a different lumen length.
- Prevent misuse of instruments whose insertion shaft length is different for different gastrointestinal tract (upper GI or lower GI).
- Useful for the periodic maintenance and analyzing the system fault, due to being able to record the history of usage about the system.
- Useful for the periodic maintenance and analyzing the system failure, due to being able to record the information about each facility.

Representative Embodiments of a Valve Controller Box

Various prior art references disclose implementation of valve controller boxes or valve control units in endoscopy systems or endoscopes. Japanese Unexamined Patent Application Publication No. 2013-90721 (Equipment for air and water feeding) discloses a simple equipment to control flow path and flow rate of air and water. Buttons on the control body 3 of the endoscope control the valves for air, water, and water jet. The water line and water jet line are interchangeable. Japanese Unexamined Patent Application Publication No. Hei 7-53148 discloses an endoscopic system to perform spray (water and air) with equipment outside of the human body. U.S. Pat. No. 8,388,522 discloses an endoscope system, program and endoscope system control method.

A technical problem associated with the aforementioned prior art references is that, since a conventional endoscope controls air, water, and suction functions using mechanical valves on its control body 3, endoscopists only can control these functions during when they are gripping the control body 3. In other words, surgeons using the surgeon console unit cannot use the air, water, and suction functions. Moreover it is not considered that plural doctors use the one endoscope system jointly.

Figure 5A:
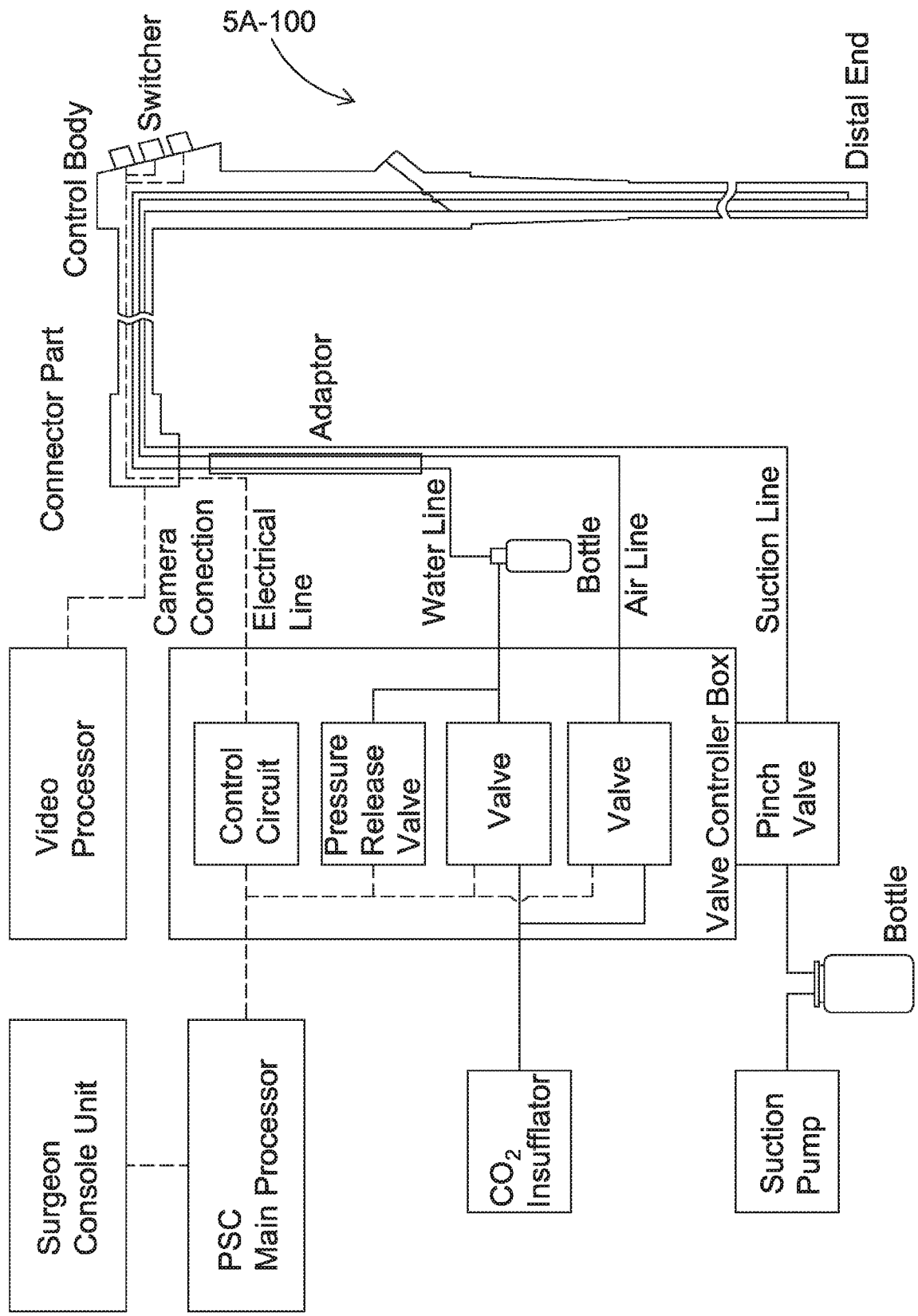
FIGS. 5A-5B are illustrations relating to a valve controller box for the endoscopy system, in accordance with an embodiment of the present disclosure.
Figure 5B:
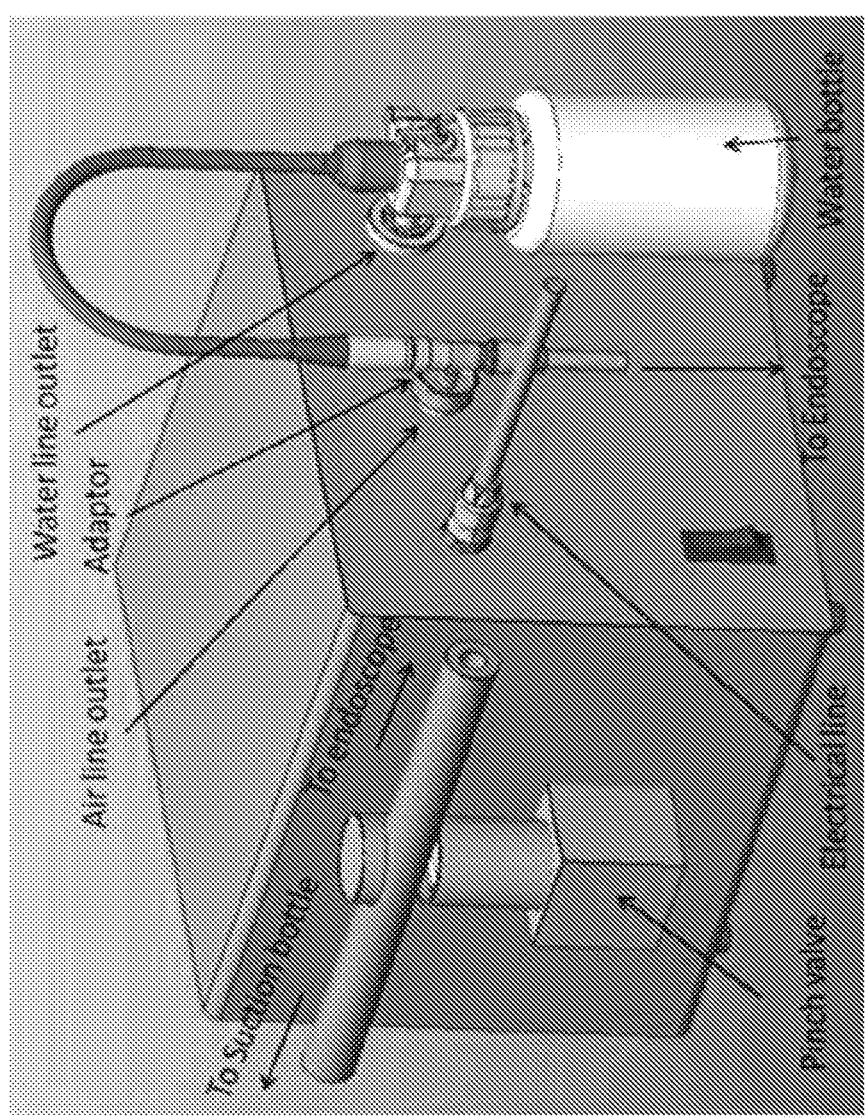

One possible solution would be to enable a surgeon, who is farther away from the endoscope to operate a console, to control valves which is to open and close air line, water line and suction line and would be to enable a endoscopist and a surgeon to use the remote controlled valves efficiently, for example such that the system makes less confliction between a endoscopist and a surgeon. The mechanical valves in the pipe lines of the endoscope are removed, and a valve controller box (VCB) which has electrical valves for air and water pipe lines and a pinch valve for suction is added to the endoscope system instead of that mechanical valves. The buttons on the control body 3 and the controller of the surgeon console unit are electrically connected to the VCB, such that these valves can be electrically controlled. Moreover, there may be indicators and/or displays to show the status of each valve, thereby mitigating risks of confusion for users. Priority can also be set to operate the VCB between switches on the control body 3 and surgeon console unit. FIG. 5A illustrates a connection diagram for embodiments of this solution, and FIG. 5B illustrates an example of the VCB.

The following describes features of the VCB.

a) Input pressure is on one line, and either air pump or carbon dioxide (CO2) insufflator is connectable thereto.
b) Input line is divided to air line and water line, and there is an electrical valve in each line.
c) Since a pressure release valve is connected to the water line, pressure can go out soon after water function goes off. Therefore, unnecessary water does not go out from a nozzle and it doesn't obstruct visualization.
d) Air and water lines of the VCB are connected to endoscope via an adaptor which can be reprocessed.
e) Since liquid passes through a valve in related prior arts Japanese Unexamined Patent Application Publication No. 2013-90721 and Japanese Unexamined Patent Application Publication No. Hei 7-53148, that pipe line needs to be reprocessed or replaceable. There is no mention to control from excepting endoscope in related prior arts Japanese Unexamined Patent Application Publication No. 2013-90721, Japanese Unexamined Patent Application Publication No. Hei 7-53148, and U.S. Pat. No. 8,388,522.
f) Suction function is controlled with a pinch valve located outside of the chassis. Generally, the tube between the endoscope and suction bottle is disposable because soil passes though that tube.
g) Electrical valves, pressure release valve, and pinch valve are connected to the control circuit. These valves are controlled with switches on the control body 3 and surgeon console unit.
h) Switches on the control body 3 are directly connected to the control circuit in the VCB. Signals from the surgeon console unit are transmitted to the control circuit in the VCB ox via the main the system (PSC Main Processor/SCU Main Processor).
i) Under a timing chart relating the air and water buttons and valves. Air function can be on during some period of time after the water button is turned off.
j) Priority is set between input from the endoscope and from the surgeon console unit side to drive the valves in the VCB.

In a first example of the priority feature, as long as a button is activated on either side, the corresponding valve works. For example, if the water feeding button is pressed on the surgeon console unit (SCU) but not on the endoscope, water will be fed. When this is the other way around, i.e. the water feeding button is pressed on the endoscope but not on the surgeon console unit, water will also be fed. Further, when the buttons on the surgeon console unit and endoscope are pressed, water will be fed as well. Suction has a priority over insufflation. This means that while the insufflation button is pressed on one side, and the suction button is pressed on the same side or on the other side, the suction command overrides the insufflation command. Multiple buttons (and thus valve control) can be activated at the same time except for the above case where suction and insufflation are activated simultaneously (and suction takes priority over insufflation). The following table illustrates a summary of the priority feature, or a priority chart, for this first example.

TABLE 2

| Priority feature example 1 | | | | | | |
|---|---|---|---|---|---|---|
| SCU water button | Endoscope water button | SCU insufflation button | Endoscope insufflation button | SCU suction button | Endoscope suction button | Result |
| Press | Press | — | — | — | — | Water feeding |
| Press | — | — | — | — | — | Water feeding |
| — | Press | — | — | — | — | Water |

TABLE 2-continued

Priority feature example 1

| SCU water button | Endoscope water button | SCU insufflation button | Endoscope insufflation button | SCU suction button | Endoscope suction button | Result |
|---|---|---|---|---|---|---|
| — | — | Press | — | Press | — | feeding Suction |
| — | — | Press | — | — | Press | Suction |
| — | — | — | Press | Press | — | Suction |
| — | — | — | Press | — | Press | Suction |

In a second example of the priority feature, when the endoscope is not docked to the docking station, suction, insufflation and lens cleaning (water feeding) can only be controlled from the endoscope. Once the endoscope is docked, suction and lens cleaning can only be controlled from the surgeon console unit. Insufflation can be controlled from either side (endoscope or surgeon console unit). Activation of multiple buttons (and thus valves) is allowed. The following table illustrates a summary of the priority feature, or a priority chart, for this second example.

TABLE 3

Priority feature example 2

| | Endoscope to docking station | |
|---|---|---|
| | Docked | Not docked |
| Control of lens cleaning (water feeding) | Surgeon console unit only | Endoscope only |
| Control of insufflation | Endoscope of surgeon console unit | Endoscope only |
| Control of suction | Surgeon console unit only | Endoscope only |

In a third example of the priority feature, when the endoscope is not docked to the docking station, suction, insufflation, and lens cleaning (water feeding) can only be controlled from the endoscope. Once the endoscope is docked, all of the functions, i.e., suction, insufflation, and lens cleaning, can only be controlled only from the surgeon console unit. There is no control from the endoscope. Activation of multiple buttons (and thus valves) is allowed. The following table illustrates a summary of the priority feature, or a priority chart, for this third example.

TABLE 4

Priority feature example 3

| | Endoscope to docking station | |
|---|---|---|
| | Docked | Not docked |
| Control of lens cleaning (water feeding) | Surgeon console unit only | Endoscope only |
| Control of insufflation | Surgeon console unit only | Endoscope only |
| Control of suction | Surgeon console unit only | Endoscope only |

In an alternative embodiment of the solution, the endoscope connector part is separated into a video processor connector part and a VCB connector part. The video processor connector includes an electrical connector for imaging and an optical fiber plug for lighting. The VCB connector is connected to the control circuit and air line directly, and to the water line via a water bottle. The video processor connector may be separable in the junction.

There are several advantageous effects in implementing this solution, listed as follows:

Spraying water comes out when both the air and water buttons are pushed, and cleaning ability is improved as compared to using just water.

If assignment is changed, spraying water comes out only when the water button is pushed.

Both the endoscopist and the surgeon can use the functions of air feeding, water feeding, and suction.

While one of the endoscopist and the surgeon is using them, the other can recognize that because it is indicated on a screen.

The users will not be confused because the VCB operation is prioritized between the endoscopist and the surgeon like as the priority features and the working status of valves is displayed on a screen.

The control sequence can remove remaining water inside of the nozzle, thereby improving the clarity of visualization.

Representative Embodiments of a Cleaning Mechanism for an Imaging-Related Lens

Figure 6A:
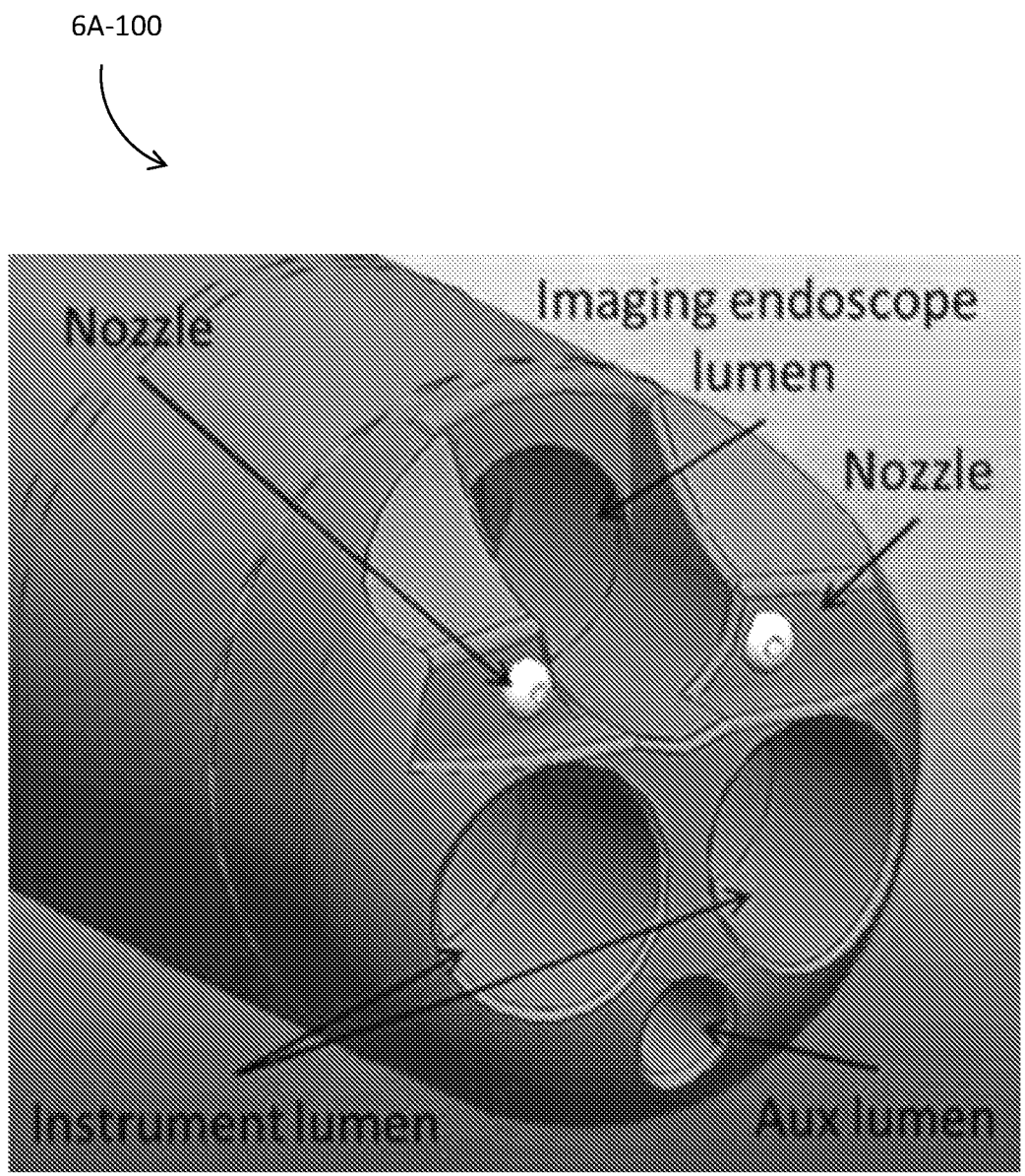
FIGS. 6A-6F are illustrations relating to a cleaning mechanism for an imaging-related lens, in accordance with an embodiment of the present disclosure.
Figure 6B:
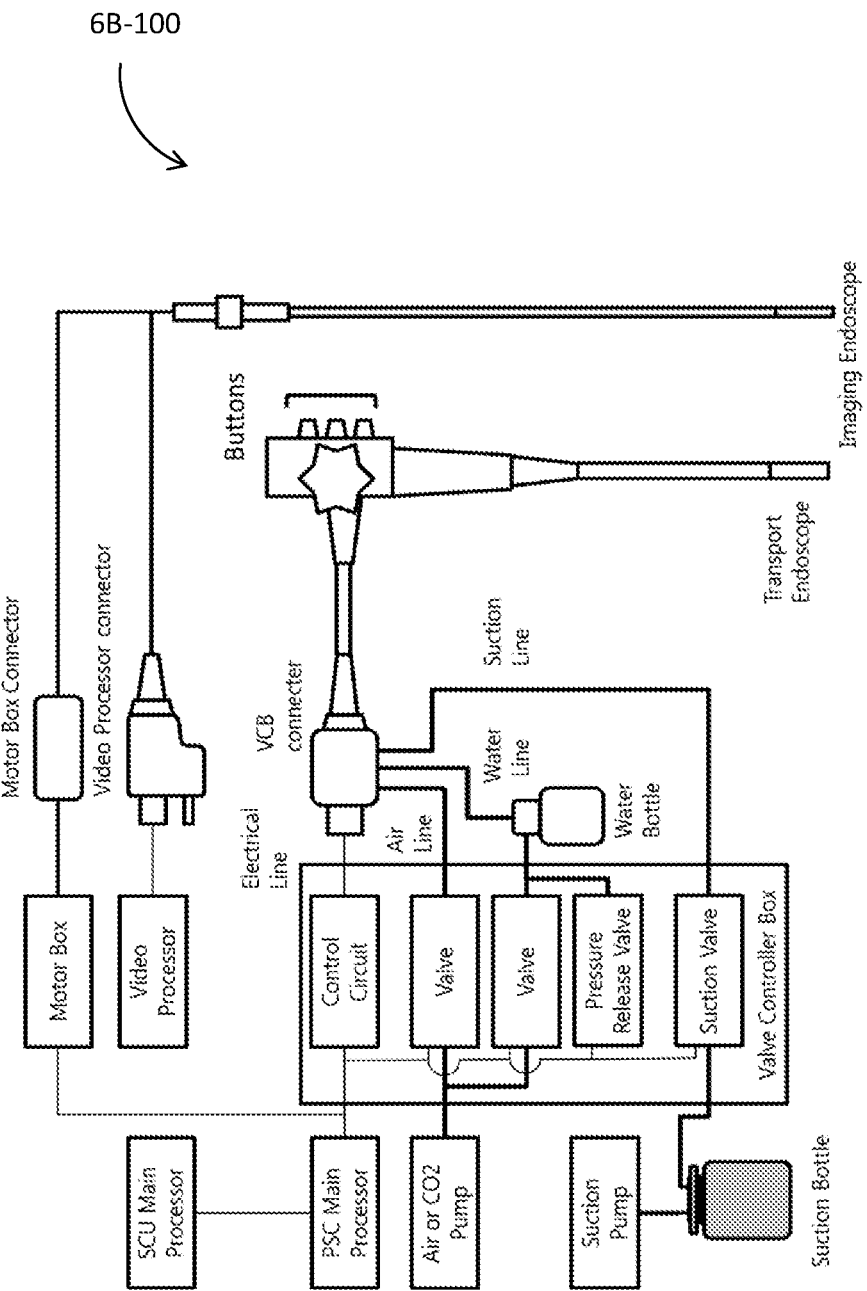
Figure 6C:
Figure 6C:
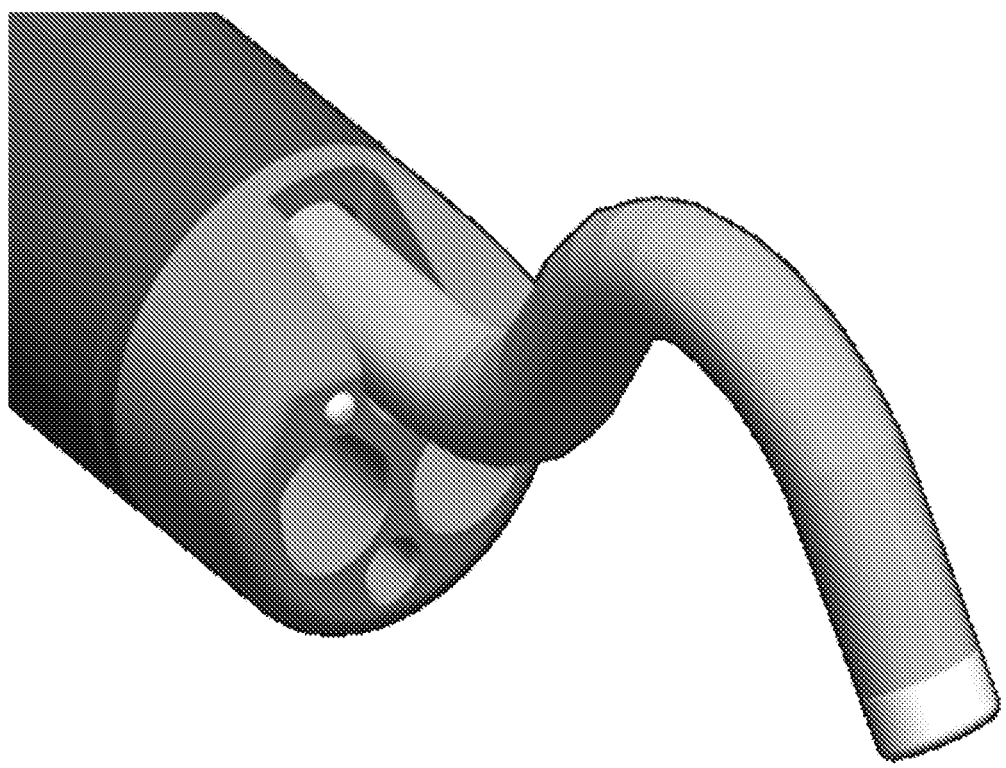
Figure 6D:
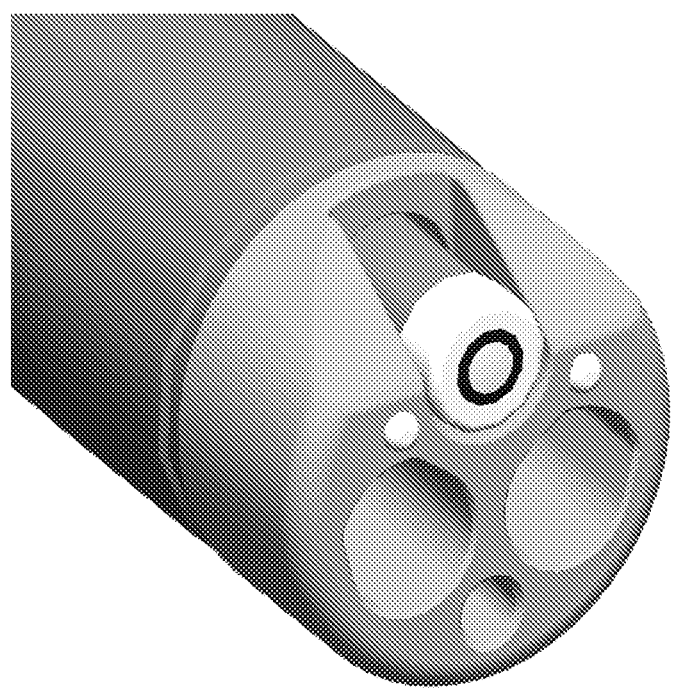
Figure 6E:
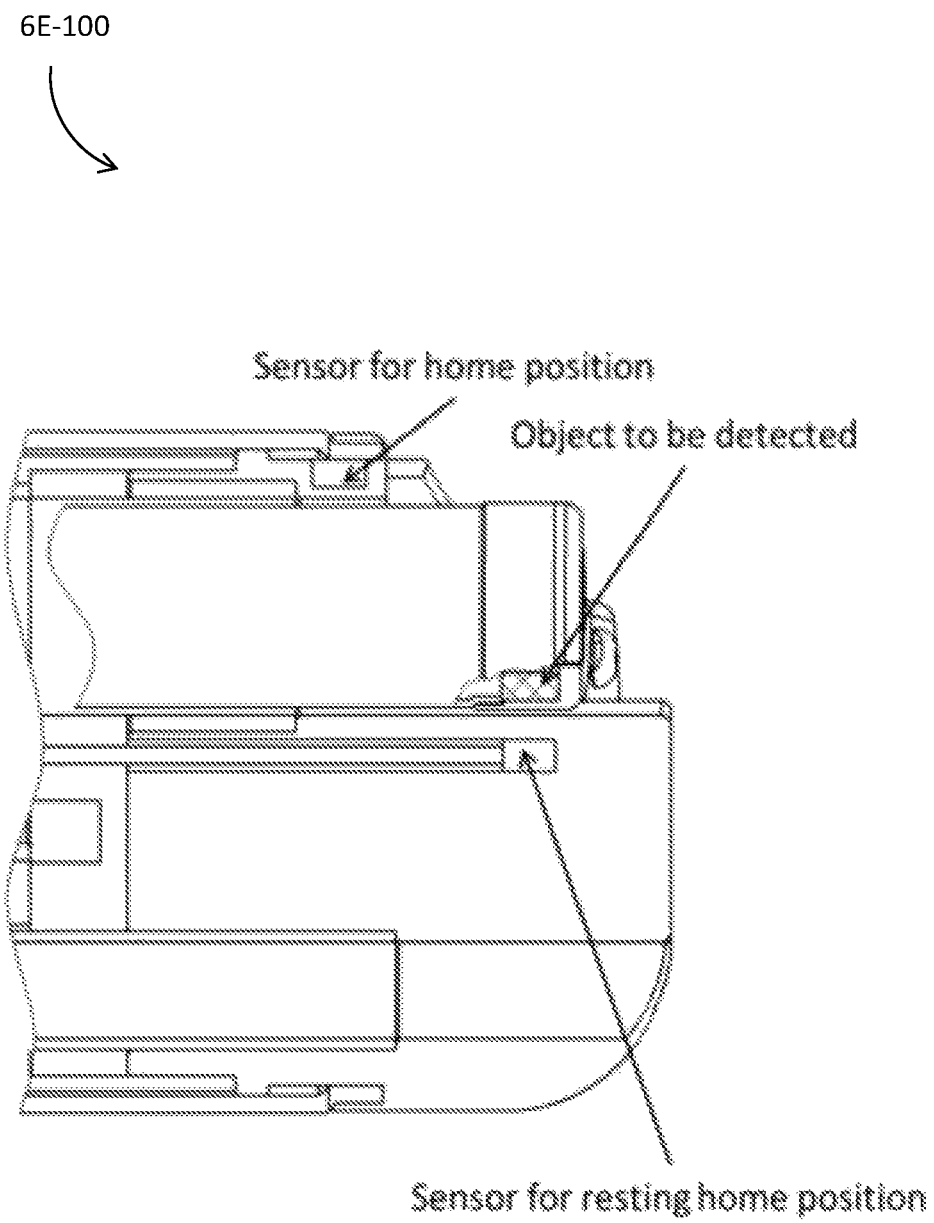
Figure 6F:
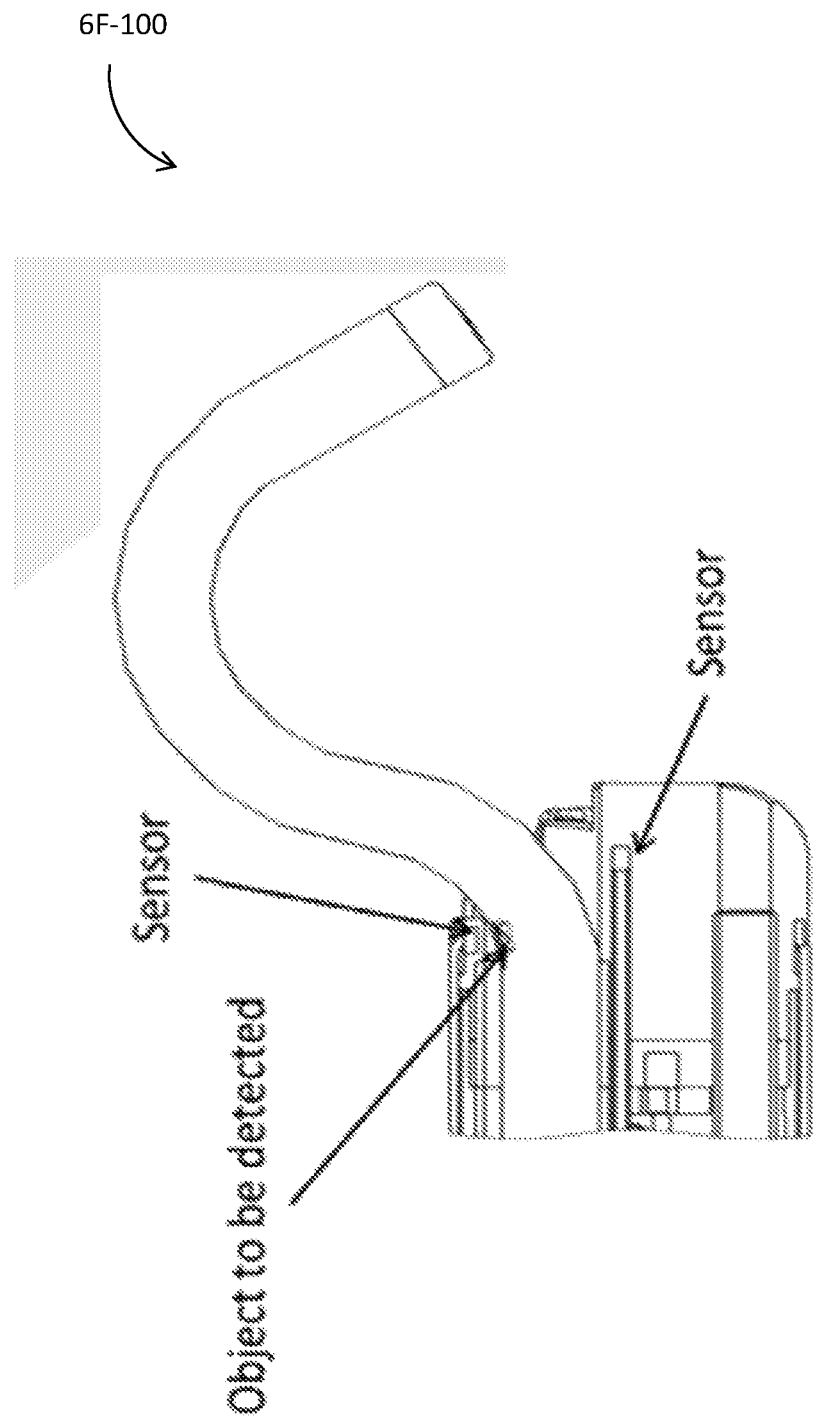

FIGS. 6A and 6C-6F illustrate the distal portion of the endoscope. FIG. 6A includes is a view of the end face 6A-100, FIG. 6B is a view of the endoscope system 6B-100, FIG. 6C is a view with the imaging instrument extended 6C-100 in the working home position, FIG. 6D is a view with the imaging instrument protracted 6D-100 in the resting home position, FIG. 6E is a cross section view showing the sensor position 6E-100 with the imaging instrument at resting home position, FIG. 6F is a cross section view showing the sensor position for working home position 6F-100.

For parent-child endoscope system, if the imaging endoscope has a pipe line for lens cleaning, the outer diameter becomes bigger, and results in the outer diameter of the transport endoscope becoming larger. Moreover, if the imaging endoscope has a pipe line for lens cleaning, the control body 3 of the imaging endoscope also gets bigger because the control body 3 needs a control system such as valves. Some relevant prior art in this regard includes Japanese Unexamined Patent Application Publication No. 2014-18563 (Guide tube for endoscope) and Japanese Unexamined Patent Application Publication No. 2014-203064 (Endoscope equipment, overtube, and optical adaptor). Like these, the overtube has the function to clean lens of imaging endoscope but these does not care about the situation which imaging endoscope is protruded from transport endoscope.

In protruded position, which is named working home position, a surgeon can get good view for surgery, but the surgeon cannot clean the lens, therefore the surgeon often has to pull the imaging endoscope to clean its lens because fats and/or other dirt splash to the lens of the imaging endoscope during use of the cautery device. Moreover, the cleaning procedure is: (i) release the bending angulation; (ii) pull the imaging endoscope and adjust to the face of transport endoscope; (iii) flush with water feeding; (iv) blow with air feeding; and (v) return to working home position. So, it has many steps.

One possible solution is to clean lens of the imaging endoscope, which does not have air and water pipe lines, in parent-child endoscope system easily and efficiently, such that the imaging endoscope only has a charge-coupled device (CCD), lens, and lighting. The transport endoscope has air and water pipe lines for lens cleaning and pipe line controller, thereby making lens cleaning possible.

On the medical equipment that has the imaging endoscope and transport endoscope, there are air and water pipe lines for lens cleaning on the distal end of transport endoscope. FIG. 6B illustrates a whole view of the transport endoscope and FIG. 6A illustrates the distal end of the transport endoscope. Referring to FIGS. 6A and 6B, the transport endoscope includes a lumen for the imaging endoscope, lumens for robotic arm, auxiliary (AUX) lumen, and air and water pipe lines. Additionally, the transport endoscope may also have water jet.

The transport endoscope comprises a bending section, flexible tube, control body 3 and valve controller box. The bending section can be controlled mechanically with a knob on the control body 3. The valve controller box connects to the transport endoscope with air pipe line, water pipe line, suction line, and electrical line for controlling the valve controller box. Further, there are valves which can be controlled by using controller of the surgeon console unit and buttons on the control body 3 of transport endoscope, in each of the pipe lines. FIG. 5A illustrates an exemplary connection diagram. If insufflator for pneumoperitoneum is used, the pipe line and valve for pneumoperitoneum line may be added, and that line is joined to the suction line (AUX lumen).

The imaging endoscope includes lighting and visualization system which has imaging sensor such as a CCD or complementary metal-oxide semiconductor (CMOS), and a lens. The imaging endoscope comprises a bending section, flexible tube part, control body 3, motorbox connector, and video processor connector. Motors that are installed in the motorbox and translation stage drive bending movement and translation.

The transport endoscope is inserted into the patient's body and reaches near the target position while the imaging endoscope is fixed at the resting home position inside the transport endoscope. Then, the imaging endoscope is commanded to move to the working home position and the surgeon performs treatments.

With the selecting switch for position change in the surgeon console unit, the imaging endoscope position can be switched to the working home position from the resting home position. Some sensors such as Hall effect sensor or optical sensor can be used for alignment between the imaging endoscope and transport endoscope.

The distal end of the imaging endoscope can be moved up and down, right and left from the working home position by the surgeon console unit according to surgeon's needs. When the lens of imaging endoscope gets dirty with fats or other dirt with the imaging endoscope is at working home position, the imaging endoscope needs to go back to the resting home position to clean the lens.

While the imaging endoscope is at the resting home position, the endoscopist can perform air and water functions by pushing the switches on the control body 3. When the imaging endoscope is at the working home position, the surgeon can clean the lens on the imaging endoscope using the controller of the surgeon console unit. The controller includes a selecting switch for position change, air button, and water button. While the imaging endoscope is at the working home position, after pushing the selecting switch, the imaging endoscope moves from working home position to the resting home position. The surgeon can clean lens with the air button and water button. After the camera view is cleaned, the imaging endoscope goes back to the working home position using the selecting switch, and then the surgeon can resume treatment.

This system may include an automatic lens cleaning mode. The controller includes a selecting switch for position change, automatic cleaning button, air button, and water button. If the surgeon pushes the automatic cleaning button when the imaging endoscope is at the working home position, the imaging endoscope moves to the resting home position, and the lens is cleaned with air and water. At this time, if necessary, the surgeon can clean the lens with the automatic cleaning button, air button, or water button. After that, the imaging endoscope goes back to the working home position with the position change switch. In one automatic lens cleaning mode, the imaging endoscope at the resting home position can move in front and behind several times with cleaning air and/or water.

In a configuration of the distal end of the transport endoscope, it can be seen that the nozzle opening can face the center of the lens. Air and water flow may be parallel with the objective lens surface of the imaging endoscope, or may be at an angle with respect to the apical surface. A cross section of the air or water pipe line, the air and water pipe lines may have lateral branch. Further, the water pipe line and air pipe line may join their respective nozzles. In this case, there may be one or more nozzles on the transport endoscope. A cross section of the air and water pipe lines can be joined into one pipe line. During automatic cleaning mode, it is changeable whether lens is cleaned with water or spray (water and air), as summarized in the following table.

TABLE 5

| Button assignments | | |
| --- | --- | --- |
| Button | Assignment 1 | Assignment 2 |
| Auto Clean | Water (after moving to the resting home position) | Spray Water and Air (after moving to the resting home position) |
| Water | Water | Water |
| Air | Air | Air |
| Position | Switch to the home position | Switch to the home position |

There are several advantageous effects in implementing this solution, listed as follows:
  Spaying (water and air) for lens cleaning is better than using air and water individually.
  While endoscopes are being inserted near to the target site, the imaging endoscope is set into the resting home position. Therefore, the endoscopist can clean a lens with the similar operation to existing endoscopes.
  After the endoscope gets near to the target site, the imaging endoscope switches to the working home position and the surgeon can keep a suitable view for treatment or surgery with triangulation.
  If the lens gets dirty due to fats and/or mucus, a series of lens cleaning steps is required, namely straightening the imaging endoscope, pulling back the imaging endoscope to the resting home position, cleaning the lens, and returning the imaging endoscope back to the working home position. This series of lens cleaning steps is time-consuming. Therefore, the automatic cleaning mode reduces the complications and complexity of the operation.
  During automatic cleaning mode, dirt on lens is removed easier because the imaging endoscope at the resting home position moves in front and behind several times with cleaning air and/or water.
  During automatic cleaning mode, dirt on lens is removed easier because air and water line have lateral branch when the imaging endoscope moves in front and behind several times with cleaning air and/or water.

During automatic cleaning mode, cleaning with spray (water and air) makes removing dirt easier.

Representative Embodiments of Arrangements of Particular Lumens

Various prior art references disclose endoscopes having channels or lumens for instruments and devices, e.g. cameras and lens. U.S. Pat. No. 6,352,503 (corresponding to Japanese Unexamined Patent Application Publication No. 2000-037348) discloses an endoscope which has three channels for manual therapeutic devices. U.S. Pat. No. 7,537,561 (corresponding to Japanese Unexamined Patent Application Publication No. 2004-194827) discloses a grasper channel located in the right-side of an objective lens, and a cautery device channel located in the bottom-side of the objective lens. One of the two illumination lens is located in the near side of the objective lens, and the other is located in the lower side of the grasper channel Japanese Unexamined Patent Application Publication No. 2013-202197 discloses a cautery device channel from which fluid can be sucked is located in the lower side of the distal end. A water jet channel is located lower than the cautery device channel and a grasper channel.

There are some technical problems associated with the aforementioned prior arts. For example, each of U.S. Pat. Nos. 6,352,503, 7,537,561, and Japanese Unexamined Patent Application Publication No. 2013-202197 requires a lot of training to users because in these systems, users need to precisely control manual therapeutic devices by endoscope angulation during endoscopic procedures such as endoscopic submucosal dissection (ESD). The water jet channel of U.S. Pat. No. 7,537,561 is located far from the grasper channel. As a result, in order to find a bleeding point, mucosa has to be released from the grasper. The water jet channel of Japanese Unexamined Patent Application Publication No. 2013-202197 is located in the bottom side of the two device channels. In this configuration, forward water flow may be blocked by the colon wall (stomach wall) when the bottom side of the distal end is contacting the inner wall.

In some embodiments, the transport endoscope does not contain an imaging endoscope, thereby keeping the outer diameter of the transport endoscope smaller. However, in some other embodiments as illustrated in FIG. 6A, an imaging endoscope comes out from the upper side of the transport endoscope distal end, and two instrument channels are located in the lower side symmetrically. The outer diameter of endoscope can be large because it has three channels for instruments and manual devices. The endoscope can be controlled intuitively by locating the two instrument channels symmetrically and the imaging channel at the upper-center. However, it affects the location of wires for endoscope bending. In other words, the upward bending wire has to be placed at the side of the imaging channel, but this causes endoscope operation to become unintuitive. Additionally, a grasper device comes out from the bottom side of the distal end, and a surgeon would lift up mucosa to the upside. As a result, the grasper device covers nearly half of the image area.

Figure 7A:
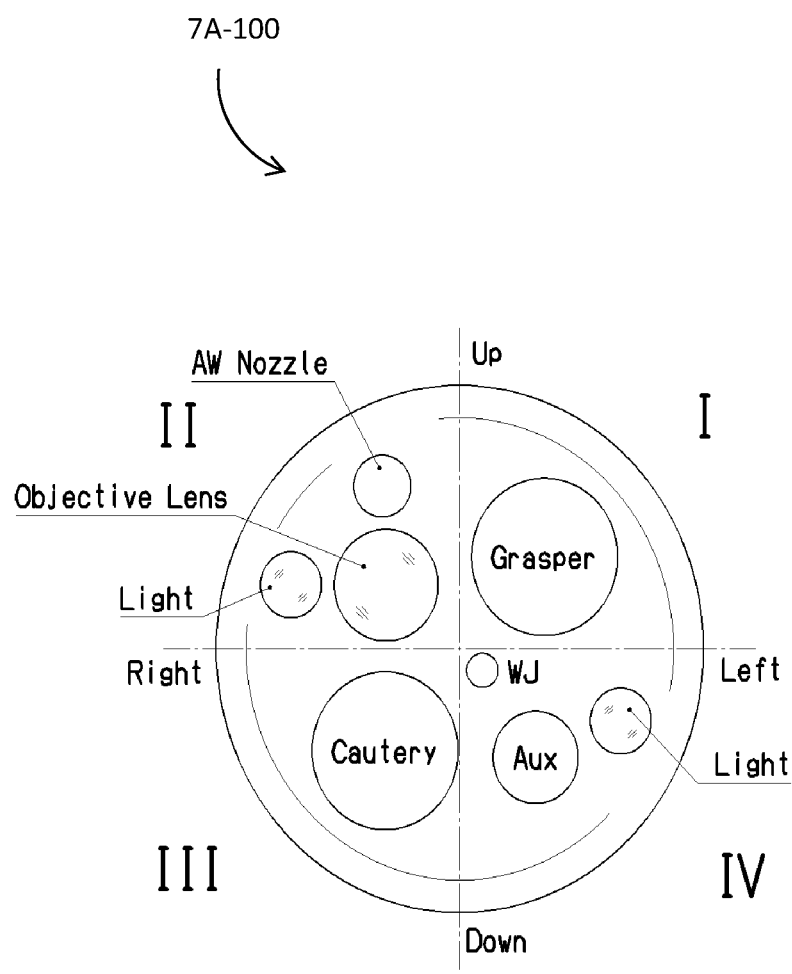
FIGS. 7A-7C are illustrations relating to arrangements of particular lumens for the endoscopy system, in accordance with an embodiment of the present disclosure.
Figure 7B:
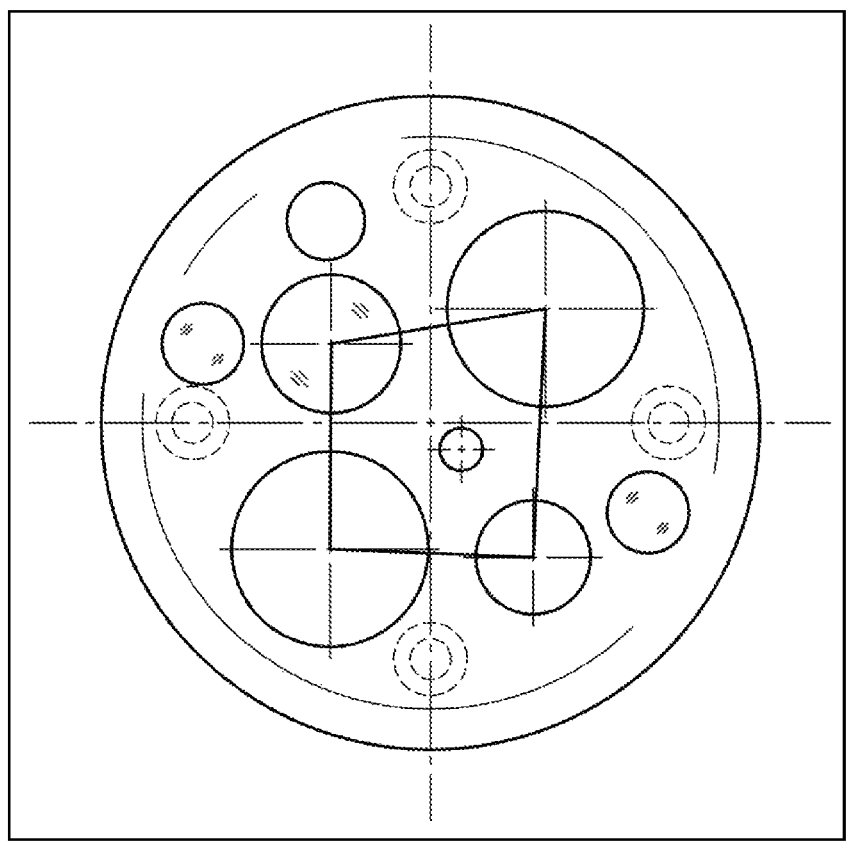
Figure 7C:
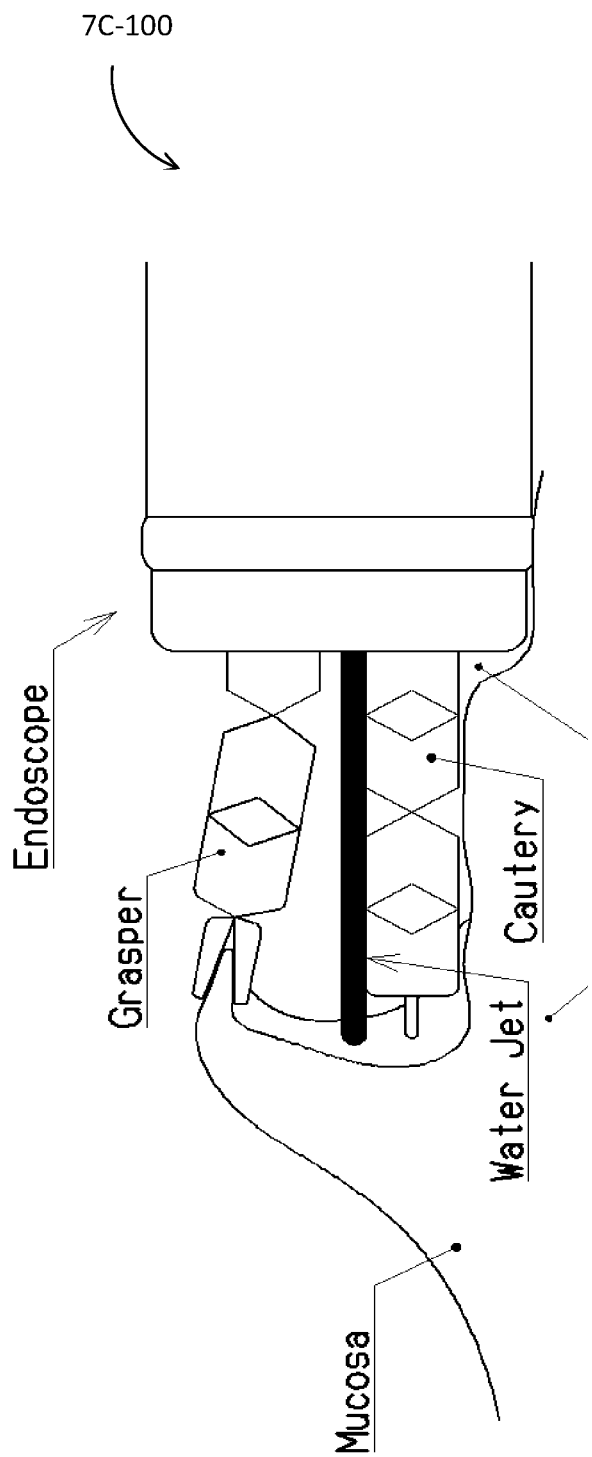

A possible solution is to divide the distal end of an endoscope into four areas (first to fourth quadrants), as illustrated in 7A. The center of a grasper instrument channel is placed in the first quadrant; a camera is placed in the second quadrant; a cautery instrument channel is placed in the third quadrant; and an auxiliary channel is placed in the fourth quadrant. In this solution, the camera is fixed to the endoscope as in conventional endoscopes in order to minimize the outer diameter. The center of a water jet channel comes inside the area made by the four centers of the camera and the channels illustrated in 7B. Illumination lens are located outside of the area, preferably in the second quadrant and the fourth quadrant in order to weaken/reduce/diminish shadows made by the grasper and cautery devices. These elements such as the camera and the channels can be also located in opposite with respect to the Up and Down axes. For the opposite location, the grasper instrument channel is placed in the second quadrant; the camera is placed in the first quadrant; the cautery instrument channel is placed in the fourth quadrant; and the auxiliary channel is placed in the third quadrant. FIG. 7B illustrates a distal end face 7B-100. FIG. 7C illustrates a side view of surgical instruments protruding from the distal end face with a water jet flow at the center 7C-100.

Referring to 7B, wires and sheaths for endoscope angulation are located at Up/Down/Right/Left directions with intervals of approximately 90 degrees. This is possible because the camera and the three channels are not located on the Up/Down/Right/Left axes. The distal end does not have to be flat. For example, the objective lens can be protruded in order to be able to observe the target site more closely. The two channels for robotic instruments may have different inner diameters depending on the instrument sizes. The shapes of the two instrument channels do not have to be circular. For example, a key way or oval/ellipsoidal shape can be used to set a rotational position of the instruments. Also, there may be more than two illumination lens.

There are several advantageous effects in implementing this solution, listed as follows:

Minimize the outer diameter of the endoscope.

Maximize the field of view, as the grasper arm does not cover a wide area of the image.

Relatively easier to find a bleeding point to treat that bleeding because the water jet channel is close to the camera, the instrument channels, and the auxiliary channel. In many cases, bleeding happens around the cautery device tip, and a hemostatic forceps and/or clip passes through the auxiliary channel Colon (stomach) wall does not block the water jet flow, as illustrated in FIG. 7C. If the water jet channel is located near the corner of the distal end such as in Japanese Unexamined Patent Application Publication No. 2013-202197, the water flow can be blocked.

Target site (lesion) is rarely covered with shadows of the grasper and cautery devices because the illuminations are located in the opposite corner of the distal end.

Relatively easier to use suction and manual devices such as injection needles, hemostatic forceps, and clips, because the auxiliary channel location is almost the same as in conventional endoscopes.

Representative Embodiments of Surgical Instrument Distal Position Sensor(s)

It is desirable from a system perspective, for the PSC Main Processor to know the precise position of the surgical instrument end effector relative to the distal tip of the endoscope. A number of factors make it difficult to control this position precisely, including but not limited to:

a) Compression and stretch in the length of the surgical instrument shaft.

b) Stretch and compression of the endoscope lumen length. This compression or stretch, which may be due to a variety of factors including, but not limited to, movement of the endoscope within the patient body as well as changes in tortuosity of the endoscope.

c) Manufacturing tolerances of the length of the endoscope lumen.

While the effects of these factors can be reduced, there will always be some error between the predicted position and the actual position of the surgical instrument at the distal tip of the endoscope. This error has many effects including, but not limited to:
 a) Non-smooth motion of the surgical instrument, confounding ease of use and dexterity for the user.
 b) Difficulty in ensuring that the surgical instrument is fully emerged from the distal tip of the endoscope before allowing the surgeon to control the surgical instrument robotically. This error can result in collisions between the surgical instrument and the walls of the endoscope lumen resulting in a reduced range of motion for the surgical instrument, which may frustrate the user.
 c) If the arm is translated sufficiently distally to ensure full emersion from the endoscope lumen, given the worst possible position error, the surgeon may be prevented from bringing the surgical instrument sufficiently close to the endoscope camera for adequate visualization of the grasped tissue.

At least one sensor or a set of sensors is located and used within the endoscope, which detects at least one target located on at least one surgical instrument. The at least one sensor or set of sensors is located sufficiently close to the distal end of the endoscope to accurately measure the true position of the distal tip of the at least one surgical instrument in at least one dimension. This sensor measurement may be used for a variety of purposes, which includes but is not limited to compensating for the error between the predicted and true positions of the surgical instrument for more precise control.

The sensor, or sensors, may detect the position of the surgical instrument in more than one dimension. For example, the sensor, or sensors, may detect the surgical instrument's translation position, or the surgical instrument's roll orientation, or any number of other positional measurements in any number of dimensional directions. Those sensors include, but not limited to, a Hall effect sensor and optical sensor.

Figure 8:
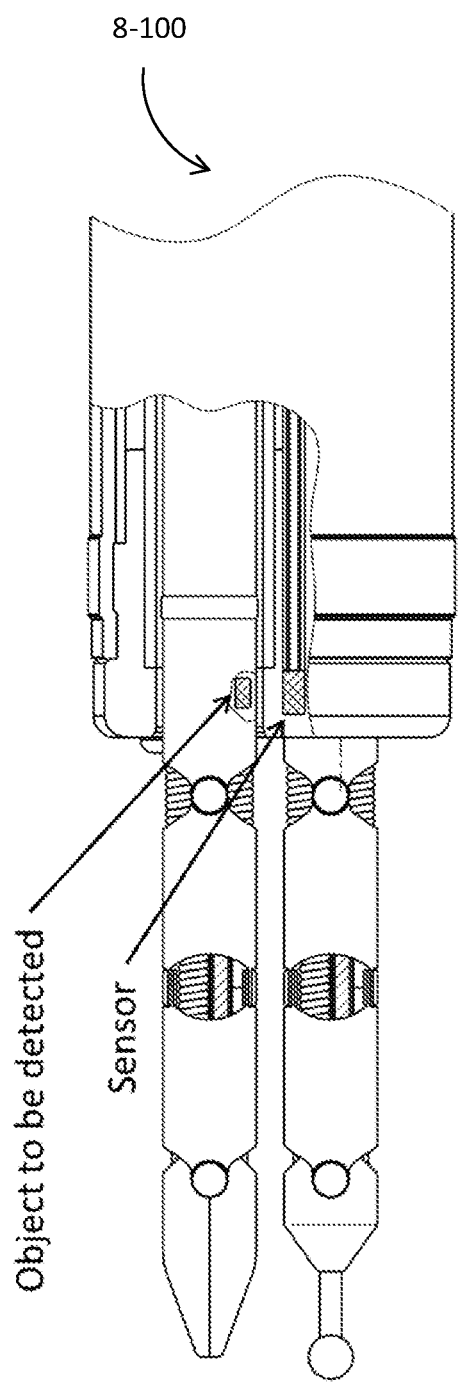
FIG. 8 is an illustration relating to surgical instrument distal position sensor(s) for the endoscopy system, in accordance with an embodiment of the present disclosure.

FIG. 8 illustrates an illustration of an embodiment of the at least one sensor and the corresponding to at least one target 8-100. Other locations and configurations of sensors and targets may be possible.

Representative Embodiments of particular embodiments of the present disclosure address at least one aspect, problem, limitation, and/or disadvantage associated with existing robotic endoscopy systems and devices. While features, aspects, and/or advantages associated with certain embodiments have been described in the present disclosure, other embodiments may also exhibit such features, aspects, and/or advantages, and not all embodiments need necessarily exhibit such features, aspects, and/or advantages to fall within the scope of the present disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope of the present disclosure.

We claim:

1. An endoscopy system with one or more surgical instruments and an endoscope,
 the endoscope comprising:
 an insertion portion having a flexible insertion tube and a distal end with a distal end face,
 wherein the insertion portion has a first surgical instrument channel, a second surgical instrument channel, and a single forward water feeding channel, wherein
 a first quadrant, a second quadrant, a third quadrant and a fourth quadrant are arranged on the distal end face, wherein:
  (i) the first quadrant and third quadrant are at opposite sides of the center of the distal end face;
  (ii) the second quadrant and the fourth quadrant are at opposite sides of the center of the distal end face;
  (iii) the quadrants are arranged in a quadrant sequence,
 and further comprising
 an objective camera lens located in the first quadrant on the distal end face,
 a first surgical instrument channel outlet located in the second quadrant on the distal end face,
 an auxiliary channel outlet located in the third quadrant on the distal end face,
 a second surgical instrument channel outlet located in the fourth quadrant,
 a single forward water feeding channel outlet for the single forward water feeding channel located on the distal end face in respect to the first and second surgical instrument channel outlets at a predetermined location, wherein the predetermined location is determined in respect to the first and second surgical instrument channel outlets and the auxiliary channel outlet; and
 wherein the one or more surgical instruments comprise
 a grasper instrument inserted into the first surgical instrument channel through to the first surgical instrument channel outlet; and
 a cautery instrument inserted into the second surgical instrument channel through to the second surgical instrument channel outlet, wherein the single forward water feeding channel outlet is configured to provide water to a target site to aid operation of the grasper instrument and/or the cautery instrument at the target site.

2. An endoscope comprising:
 an insertion portion having a flexible insertion tube and a distal end with a distal end face, wherein
 the insertion portion has a first surgical instrument channel, a second surgical instrument channel, wherein
 a first quadrant, a second quadrant, a third quadrant and a fourth quadrant are arranged on the distal end face:
  (i) wherein the first quadrant and third quadrant are at opposite sides of the center of the distal end face;
  (ii) wherein the second quadrant and the fourth quadrant are at opposite sides of the center of the distal end face; and
  (iii) wherein the quadrants are arranged in a quadrant sequence, wherein
 an objective camera lens is located in the first quadrant on the distal end face, and wherein a first surgical instrument channel outlet is located in the second quadrant on the distal end face, and
 wherein an auxiliary channel outlet is located in the third quadrant on the distal end face, and
 wherein a second surgical instrument channel outlet is located in the fourth quadrant, and
 wherein the first and second surgical instrument channels are configured, in operation, to have inserted therethrough to the respective first and second surgical instrument channel outlets a grasper instrument and a cautery instrument for operation at a target site, and wherein a single forward water feeding channel outlet for a single forward water feeding channel is located on the distal end face in respect to the first and second surgical instrument channel outlets at a predetermined location, wherein the predetermined location is determined in respect to the first and second surgical instrument channel outlets to, in operation, enable the single forward water feeding channel to provide water to the target site to aid in control of target site bleeding during the operation of the grasper instrument and/or the cautery instrument at the target site, and wherein an air/water nozzle is co-located with the objective camera lens in the first quadrant and configured to, in operation, clean the objective camera lens.

3. The endoscope of claim 2, wherein the quadrant sequence is selected from the group consisting of:

a clockwise sequence looking into the distal end face and starting the quadrant sequence from the objective camera lens; and a counter-clockwise sequence looking into the distal end face and starting the quadrant sequence from the objective camera lens.

4. The endoscope of claim 2, further comprising at least one light on an outer diameter area of the four quadrants, wherein the outer diameter area is outside a quadrangle defined by the centers of:

(a) the objective camera lens;
(b) the first surgical instrument channel outlet;
(c) the auxiliary channel outlet; and
(d) the second surgical instrument channel outlet.

5. The endoscope of claim 4, wherein the at least one light comprises a pair of lights, the pair of lights arranged on opposite sides of the distal end face.

6. An endoscopy system comprising the endoscope of claim 2 and one or more surgical instruments.

* * * * *